US007999149B2

(12) United States Patent
Phillips et al.

(10) Patent No.: US 7,999,149 B2
(45) Date of Patent: Aug. 16, 2011

(54) VASCULAR-PREFERRED PROMOTER SEQUENCES AND USES THEREOF

(75) Inventors: Jonathan Phillips, Auckland (NZ); Clare Eagleton, Auckland (NZ)

(73) Assignee: Arborgen, LLC, Summerville, SC (US)

( * ) Notice: Subject to any disclaimer, the term of this patent is extended or adjusted under 35 U.S.C. 154(b) by 260 days.

(21) Appl. No.: 12/081,845

(22) Filed: Apr. 22, 2008

(65) Prior Publication Data

US 2008/0320612 A1 Dec. 25, 2008

Related U.S. Application Data

(62) Division of application No. 10/703,091, filed on Nov. 7, 2003, now Pat. No. 7,365,186.

(60) Provisional application No. 60/428,287, filed on Nov. 22, 2002.

(51) Int. Cl.
 C12N 15/82 (2006.01)
 C12N 15/00 (2006.01)
 C12N 15/11 (2006.01)
 C12N 15/29 (2006.01)
 C12N 15/63 (2006.01)
 A01H 5/00 (2006.01)

(52) U.S. Cl. ........ 800/287; 800/278; 800/284; 800/290; 800/295; 435/320.1; 435/468; 536/23.1; 536/24.1

(58) Field of Classification Search .................. None
 See application file for complete search history.

(56) References Cited

U.S. PATENT DOCUMENTS

| | | | |
|---|---|---|---|
| 4,458,066 A | 7/1984 | Caruthers et al. | |
| 5,412,067 A | 5/1995 | Shinoda et al. | |
| 5,451,514 A | 9/1995 | Boudet et al. | |
| 5,510,474 A | 4/1996 | Quail et al. | |
| 5,545,451 A | 8/1996 | Haung et al. | |
| 5,565,340 A | 10/1996 | Chenchik et al. | |
| 5,639,952 A | 6/1997 | Quail et al. | |
| 5,656,496 A | 8/1997 | Quail et al. | |
| 5,750,385 A | 5/1998 | Shewmaker et al. | |
| 5,759,822 A | 6/1998 | Chenchik et al. | |
| 5,824,857 A | 10/1998 | Beachy | |
| 5,910,415 A | 6/1999 | Hodges et al. | |
| 6,051,757 A | 4/2000 | Barton et al. | |
| 6,054,574 A | 4/2000 | Quail et al. | |
| 6,132,970 A | 10/2000 | Stemmer | |
| 6,187,994 B1 | 2/2001 | Baszcynski et al. | |
| 6,204,434 B1* | 3/2001 | Bloksberg et al. | 800/290 |
| 6,225,529 B1 | 5/2001 | Lappegard et al. | |
| 6,380,459 B1 | 4/2002 | Perera et al. | |
| 6,410,718 B1 | 6/2002 | Bloksberg et al. | |
| 6,506,559 B1 | 1/2003 | Fire et al. | |
| 6,518,485 B1 | 2/2003 | Connett-Porceddu et al. | |
| 6,596,925 B1* | 7/2003 | Perera et al. | 800/278 |
| 2003/0101478 A1 | 5/2003 | Perera et al. | |
| 2004/0163146 A1 | 8/2004 | Phillips et al. | |
| 2005/0026162 A1 | 2/2005 | Perera et al. | |
| 2005/0244968 A1 | 11/2005 | Perera et al. | |

FOREIGN PATENT DOCUMENTS

| | | |
|---|---|---|
| EP | 271988 | 6/1988 |
| EP | 0120516 B1 | 10/1991 |
| EP | 0154204 B1 | 1/1994 |
| WO | WO 92/04449 | 3/1992 |
| WO | WO 93/19189 | 9/1993 |
| WO | WO 94/23044 | 10/1994 |
| WO | WO 95/00450 | 1/1995 |
| WO | WO 97/47756 | 12/1997 |
| WO | WO 99/61631 | 12/1999 |
| WO | WO 00/23597 A | 4/2000 |
| WO | WO 00/58474 | 10/2000 |
| WO | WO 01/20008 A | 3/2001 |
| WO | WO 01/98485 | 12/2001 |
| WO | WO 01/98485 A1 | 12/2001 |
| WO | WO 02/44337 | 6/2002 |
| WO | WO 2004/108903 | 12/2004 |
| WO | WO 2005/001051 A | 1/2005 |

OTHER PUBLICATIONS

U.S. Appl. No. 60/476,222, filed Jun. 6, 2003, Chang et al.
Adang, et al., *Plant Mol. Biol.*, vol. 21, pp. 1131, (1993).
"Crop Species", Handbook of Plant Cell Culture, 1990 UCLA Symposium on Molecular Strategies for Crop Improvement, 3 pages.
Altschul, et al., "Gapped BLAST and PSI-BLAST: a new generation of protein database search programs", *Nucleic Acids Res.*, vol. 25, pp. 3389-3402, (1997).
Altschul SF, et al., "Basic Local Alignment Search Tool", J. Mol. Biol., Academic Press Limited, Oct. 5, 1990, vol. 215, No. 3, pp. 403-410.
Aronen, Tuija, Genetic transformation of Scots pine (*Pinus sylvestris* L.), Dissertation Metsäntutkimuslaitoksen tiedonantoja 595, 1996, pp. 8-53.
Ausubel, et al., (eds.), "Current Protocols in Molecular Biology", (John Wiley & Sons, Inc.), (1990).
Ausubel, et al., (eds.), "Short Protocols in Molecular Biology", 3rd ed, (John Wiley & Sons, Inc.), (1995).
Ausubel, et al., section 2.9, supplement, vol. 27, (1994).
Bambot, et al., "PCR Methods and Applications", vol. 2, p. 266, (1993).
Baucher et al., "Red Xylem and Higher Lignig Extractability by Down-Regulating a Cinnamyl Alcohol Dehydrogenase in Poplar," Plant Physiol., 1996, vol. 112, pp. 1479-1490.
Beaucage et al., "Deoxynucleoside phosphoramidites—a new class of key intermediates for deoxypolynucleotide synthesis," Tetrahedron Letters, vol. 22, No. 20, 1981, pp. 1859-1862.
Bevan et al., "Tissue- and cell-specific activity of a phenylalanine ammonia-lyase promoter in transgenic plants," The EMBO Journal, 1989, vol. 8, No. 7, pp. 1899-1906.
Bolton ET, et al., "A General Method for the Isolation of RNA Complementary to DNA", Biochemistry: Bolton and McCarthy, Proc. Natl. Acad. Sci., 1962, vol. 48, pp. 1390-1397.
Bonner Ti, et al., "Reduction in the Rate of DNA Reassociation by Sequence Divergence", Journal of Molecular Biology, Mar. 15, 1973, vol. 81, pp. 123-135.

(Continued)

Primary Examiner — Brent T Page
(74) Attorney, Agent, or Firm — Foley & Lardner LLP

(57) ABSTRACT

Plant polynucleotide promoter sequences are provided, together with DNA constructs comprising the inventive polynucleotide. Methods for using the inventive constructs for regulating gene expression are provided, along with transgenic plants comprising the inventive constructs.

16 Claims, 10 Drawing Sheets

OTHER PUBLICATIONS

Bugos et al., "cDNA cloning, sequence analysis and seasonal expression of lignin-bispecific caffeic acid/5-hydroxyferulic acid O-methyltransferase of aspen," Plant Molecular Biology, vol. 17, 1991, pp. 1203-1215.

Chang, et al., *Plant Molecular Biology Reporter*, vol. 11, pp. 113-116, (1993).

Christensen AH, et al., "Ubiquitin Promoter-based Vectors for High Level Expression of Selectable and/or Screenable Marker Genes in Monocotyledonous Plants", Transgenic Research, Chapman & Hall, May 1996, vol. 5, No. 3, pp. 213-218.

Coleman H, et al., "Increased Growth and Yield by Altered Carbohydrate Allocation", Intl. Union of Forestry Research Organizations Biennial Conference in Umea, Sweden, Jun. 2003, 1 page.

D'Halluin K, et al., "Transgenic Maize Plants by Tissue Electroporation", The Plant Cell, 1992 Society of Plant Physiologists, Dec. 1992, vol. 4, pp. 1495-1505.

Daniell H, et al., "Containment of Herbicide Resistance Through Genetic Engineering of the Chloroplast Genome", Apr. 1998, Nature Biotechnology, vol. 16, pp. 345-348.

Datta et al., "Nucleotide sequence of a gene encoding soybean repetitive praline-rich protein 3," Plant Molecular Biology, 1990, pp. 285-286, vol. 14, Kluwer Academic Publishers, Belgium.

Dharmawardhana et al., "cDNA Cloning and Heterologous Expression of Coniferin beta-glucosidase", Plant Molecular Biology, International Society for Plant Molecular Biology, Kluwer Academic Publishers, May 1999, vol. 40, No. 2, pp. 365-372.

Dillon, et al., "Use of the Polymerase Chain Reaction for the Rapid Construction of Synthetic Genes", in Methods in Molecular Biology, PCR Protocols: Current Methods and Applications, White (ed.), vol. 15, pp. 263-268, (Humana Press, Inc.), (1993).

Ellis et al., "Stable transformation of *Picea glauca* by Particle Acceleration," Biotechnology, vol. 11, Jan. 1993, pp. 84-89.

Feuillet et al., "Tissue- and Cell-Specific Expression of a Cinnamyl Alcohol Dehydrogenase Promoter in Transgenic Poplar Plants", Plant Molecular Biology, International Society for Plant Molecular Biology, Kluwer Academic Publishers, Feb. 1995, vol. 27, No. 4, pp. 651-667.

Fraley RT, et al., "Expression of Bacterial Genes in Plant Cells", Proc. Natl. Acad. Sci. USA, Monsanto Company, Aug. 1983, vol. 80, pp. 4803-4807.

Gleave et al., "A versatile binary vector system with a T-DNA organizational structure conducive to efficient integration of cloned DNA into the plant genome," Plant Molecular Biology, vol. 20, 1992, pp. 1203-1207.

Golovkin et al., "Production of transgenic maize plants by direct DNA uptake into embryogenic protoplasts," Plant Science, 1993, pp. 41-52, vol. 90, Elsevier Scientific Publishers Ireland Ltd.

Gowri et al., Stress Responses in Alfalfa (*Medicago sativa* L.), Plant Physiol., vol. 97, 1991, pp. 7-14.

Grand et al., "Inhibition of Cinnamyl-alcohol-dehydrogenase Activity and Lignin Synthesis in Poplar (*Populus X euramericana* Dode) Tissues by Two Organic Compounds", Planta, Springer-Verlag, 1985, vol. 163, No. 2, pp. 232-237.

Grima-Pettenati et al., "Lignin Genetic Engineering Revisited", Plant Science, Elsevier Science Ireland Ltd., 1999, vol. 145, pp. 51-65.

Hatton D, et al., "Two Classes of CIS Sequences Contribute to Tissue-Specific Expression of a PAL2 Promoter in Transgenic Tobacco", The Plant Journal, 1995, vol. 7, No. 6, pp. 859-876.

Hauffe KD, et al., "Combinatorial Interactions Between Positive and Negative CIS-acting Elements Control Spatial Patterns of 4CL-1 Expression in Transgenic Tobacco", The Plant Journal, 1993, vol. 4, No. 2, pp. 235-253.

Hayashimoto A, et al., "A Polyethylene Glycol=Mediated Protoplast Transformation System for Production of Fertile Transgenic Rice Plants", Plant Physiology, The American Society of Plant Physiologists, Jul. 1990, vol. 93, No. 3, pp. 857-863.

Herrara-Estrella L, et al., Expression of Chimaeric Genes Transferred into Plant Cells Using a Ti-plasmid-derived Vector, Nature, International Weekly Journal of Science, Macmillan Journals Ltd., May 19-25, 1983, vol. 303, No. 5914, pp. 209-213.

Hinchee et al., "Production of Transgenic Soybean Plants Using Agrobacterium-Mediated DNA Transfer", Bio/Technology, The International Monthly for Industrial Biology, Aug. 1988, vol. 6, pp. 915-922.

Holowachuk, et al., "PCR Methods Appl.", vol. 4, p. 299, (1995).

Horsch RB, et al., "A Simple and General Method for Transferring Genes into Plants", Science 227, Mar. 1985, pp. 1229-1231.

Horsch RB, et al., Rapid Assay of Foreign Gene Expression in Leaf Discs Transformed by *Agrobacterium tumefaciens*: Role of T-DNA Borders in the Transfer Process, Proc. Natl. Acad. Sci. USA, Jun. 1986, vol. 83, pp. 4428-4432.

Huang et al., "*Agrobacterium rhizogenes*-mediated genetic transformation and regeneration of a conifer: *Larix decidua*," In Vitro Cell. Dev. Biol., vol. 27P, Oct. 1991, pp. 201-207.

Izawa et al., "Plant bZIP Protein DNA Binding Specificity," J. Mol. Biol., vol. 230, 1993, pp. 1131-1144.

Jefferson RA, et al., GUS Fusions: Beta-glucuronidase as a Sensitive and Versatile Gene Fusion Marker in Higher Plants, The EMBO Journal, IRL Press Limited, Dec. 20, 1987, vol. 6, No. 13, pp. 3901-3907.

Jefferson, "Assaying Chimeric Genes in Plants: The GUS Gene Fusion System", Plant Molecular Biology Reporter, Plant Breeding Institute, 1987, vol. 5, No. 4, pp. 387-405.

Kawaoka et al., "Functional analysis of tobacco LIM protein Ntlin1 involved in lignin biosynthesis," The Plant Journal, vol. 22, No. 4, 2000, pp. 289-301.

Keller B, et al., "Vascular expression of the *grp1.8* promoter is controlled by three specific regulatory elements and one unspecific activating sequence", Plant Molecular Biology, International Society for Plant Molecular Biology, Kluwer Academic Publishers, Oct. 1994, vol. 26, No. 2, pp. 747-756.

Keller et al., "Vascular Expression of a Bean Cell Wall Glycine-rich Protein—beta—glucuronidase Gene Fusion in Transgenic Tobacco", The Embo Journal, IRL Press Limited, May 1989, vol. 8, No. 5, pp. 1309-1314.

Klee HJ, et al., "Vectors for Transformation of Higher Plants", Bio/Technology, Jul. 1985, vol. 3, pp. 637-642.

Klein TM, et al., "Factors Influencing Gene Delivery into *ZEA Mays* Cells by High-Velocity Microprojectiles, Bio/Technology," BioActive Compounds From Algae May 1988, vol. 6, pp. 559-563.

Kononowicz H,, Subdomains of the Octopine Synthase Upstream Activating Element Direct Cell-Specific Expression in Transgenic Tobacco Plants, The Plant Cell, 1992 American Society of Plant Physiologists, Jan. 1992, vol. 4, pp. 17-27.

Lacombe et al., Characterization of *cis*-elements Required for Vascular Expression of the *Cinnamoyl CoA Reductase* Gene and for Protein DNA Complex Formation, The Plant Journal, 2000 Blackwell Science Ltd., vol. 23, No. 5, pp. 663-676.

Levy I. et al., Modification of Polysaccharides and Plant Cell Wall by endo-1,4-beta-glucanase and Cellulose Binding Domains, Biomolecular Engineering, 2002 Elsevier Science B. V., vol. 19, pp. 17-30.

Leyva A, et al., "*cis*-Element Combinations Determine Phenylalanine Ammonia-Lyase Gene Tissue-Specific Expression Patterns", The Plant Cell, 1992 American Society of Plant Physiologists, Mar. 1992, vol. 4, pp. 263-271.

Loopstra, et al., *Plant Mol Biol.*, vol. 27, pp. 277-291, (1995).

Marita et al., "NMR characterization of lignins from transgenic poplars with suppressed caffeic acid O-methyltransferase activity," J. Chem. Soc. Perkin Trans. 1, 2001, pp. 2939-2945.

Martin C, et al., "MYB Transcription Factors in Plants", Trends in Genetics, 1997 Elsevier Science Ltd., Feb. 1997, vol. 13, No. 2, pp. 67-73.

Matsuda et al., "Partial Male Sterility in Transgenic Tobacco Carrying Antisense and Sense *PAL* cDNA Under the Control of a Tapetum-Specific Promoter", Plant & Cell Physiology, The Japanese Society of Plant Physiologists, Mar. 1996, vol. 37, No. 2, pp. 215-222.

McCarthy et al., "The Rate of Change of DNA in Evolution," *In Evolution of Genetic Systems*, 1972, pp. 1-43, H.H. Smith (ed.), Brookhaven Symposium in Biology No.23, Gordon and Breach, New York.

McElroy D, et al., "Isolation of an Efficient Actin Promoter for Use in Rice Transformation", The Plant Cell, 1990 American Society of Plant Physiologists, Feb. 1990, vol. 2, pp. 163-171.

Menkens et al., "The G-box: a ubiquitous regulatory DNA element in plants bound by the GBF family of bZIP proteins," TIBS, Dec. 1995, pp. 506-510.

Miki BL, et al., "Procedures for Introducing Foreign DNA into Plants", Methods in Plant Molecular Biology and Biotechnology, CRC Press, 1993, pp. 67-88.

Needham-Vandevanter et al., "Characterization of an adduct between CC-1065 and a defined oligodeoxynucleotide duplex," Nucleic Acids Research, vol. 12, No. 15, 1984, pp. 6159-6168.

Neustaedter DA, et al., "A Novel Parsley 4CL1 cis-element is Required for Developmentally Regulated Expression and Protein DNA Complex Formation", The Plant Journal, 1999, Blackwell Science Ltd., vol. 18, No. 1, pp. 77-88.

No EG, et al., "Sequences Upstream and Downstream of Two Xylem-Specific Pine Genes Influence Their Expression", Plant Science, 2000 Elsevier Science, vol. 160, pp. 77-86.

Paddison P, et al., "Short Hairpin RNAs (shRNAs) Induce Sequence-Specific Silencing in Mammalian Cells", Genes & Development, Cold Spring Laboratory Press, 2002, vol. 16, pp. 948-958.

Pearson, et al., Proc. Natl. Acad. Sci., vol. 85, pp. 2444-2448, (1988) USA.

Pearson, Methods in Enzymol., vol. 183, pp. 63-98, (1990).

Perera, J.R. et al., US-09-598401C-113, sequence alignment between SEQ ID No. 3 and SEQ ID No. 113 of U.S. Patent No. 6,596,295, issued Jul. 2003.

Kim, Y et al. A. 20 nucleotide element is essential for the nopaline synthase (nos) promoter activity. Plant Mol Biol., Jan. 24, 1994(1), pp. 105-117.

Buzeli R.A. et al., Tissue-Specific regulation of BIP genes; a cis-acting regulatory domain is required for BIP Promoter Activity in Plant Meristems, Plant Mol Biol., Nov. 2002 (50)(4-5); pp. 757-771.

Gillespie, D., The Magic and Challenge of DNA Probes as Diagnostic Reagents, Vet. Microbiol., Sep. 1990:24 (3-4); 217-33.

Polvere R.I., et al., GenBank Accession No. U88240, Trichinella spiralis hypothetical ORF 2.20 mRNA, partial cds, Mar. 4, 1997.

Potrykus et al., "Direct Gene Transfer to Cells of a Graminaceous Monocot", Mol. Gen. Genet, Springer-Verlag, 1985, vol. 199, pp. 183-188.

Ringli et al., "Specific interaction of the tomato bZIP transcription factor VSF-1 with a non-palindromic DNA sequence that controls vascular gene expression," Plant Molecular Biology, vol. 37, 1998, pp. 977-988.

Rogers SG, et al., "Improved Vectors for Plant Transformation: Expression Cassette Vectors and New Selectable Markers", Methods in Enzymology, Recombinant DNA, Part D, Academic Press,1987, Inc., vol. 153, pp. 253-277.

Salehuzzaman et al., "Isolation and Characterization of a cDNA Encoding Granule-Bound Starch Synthase in Cassava (*Manihot esculenta* Crantz) and its Antisense Expression in Potato", Plant Molecular Biology, Kluwer Academic Publishers, 1993, vol. 23, pp. 947-962.

Sambrook & Russel, "Molecular Cloning: A Laboratory Manual", 3$^{rd}$ Ed., Cold Spring Harbor Laboratory Press, Cold Spring Harbor, NY, (2001).

Schmidhauser et al., "Regions of Broad-Host-Range Plasmid RK2 Involved in Replication and Stable Maintenance in Nine Species of Gram-Negative Bacteria," Journal of Bateriology, Oct. 1985, pp. 446-455, vol. 164, No. 1, American Society for Microbiology.

Shani Z, al., "Cellulose Binding Domain Increases Cellulose Synthase Activity in *Acetobacter xylinum*, and Biomass of Transgenic Plants", Plant Biotechnology and In Vitro Biology in the 21$^{st}$ Century, Proceedings of the IXth International Congress of the International Association of Plant Tissue Culture and Biotechnology Jerusalem, Isreal, Jun. 14-19, 1998, Kluwer Academic Publishers, 1999, pp. 213-218.

Sibley et al., "The Phylogeny and Classification of the Passerine Birds, Based on Comparisons Genetic Material, DNA," *ACTA XVIII Congressus Internationalis Ornithologici*, Aug. 16-24, 1982, pp. 83-121, vol. 1.

Smith et al., "Antisense RNA Inhibition of Polygalacturonase Gene Expression in Transgenic Tomatoes", Nature, Aug. 1988, vol. 334, No. 25, pp. 724-726.

Smith et al., "Inheritance and Effect on Ripening of Antisense Polygalacturonase Genes in Transgenic Tomatoes", Plant Molecular Biology, International Society for Plant Molecular Biology, Kluwer Academic Publishers, Mar. 1990, vol. 14, No. 3, pp. 369-379.

Smith, et al., Nature, vol. 334, pp. 724-726, (1988).

Smith, et al., Plant Mol. Biol., vol. 14, pp. 369-379, (1990).

Stalker DM, et al., "Purification and Properties of a Nitrilase Specific for the Herbicide Bromoxynil and Corresponding Nucleotide Sequence Analysis of the b*xn* Gene*", The Journal of Biological Chemistry, The American Society for Biochemistry and Molecular Biology, Inc., May 5, 1988, vol. 263, No. 13, pp. 6310-6314.

Thillet J, al., "Site-Directed Mutagenesis of Mouse Dihydrofolate Reductase", The Journal of Biological Chemistry, The American Society for Biochemistry and Molecular Biology, Inc., Sep. 1968, vol. 263, No. 25, pp. 12500-12508.

Torres-Schumann S, al., "In Vitro Binding of the Tomato bZIP Transcriptional Activator VSF-1 to a Regulatory Element that Controls Xylem-Specific Gene Expression", The Plant Journal, 1996, vol. 9, No. 3, pp. 283-296.

Udovicic, G.I. et al., Phylogeny of Eucalyptus and Angophora 5S rDNA Based on Spacer Sequence Data, Molecular Phylogenetics and Evolution 4 (1995), pp. 247-256.

Van Der Meer et al., "Antisense Inhibition of Flavonoid Biosynthesis in Petunia Anthers Results in Male Sterility", The Plant Cell, American Society of Plant Physiologists, Mar. 1992, vol. 4, pp. 253-262.

Van Devanter, et al., Nucleic Acids Res., vol. 12, pp. 6159-6168, (1984).

Vasil V, al., "Herbicide Resistant Fertile Transgenic Wheat Plants Obtained by Microprojectile Bombardment of Regenerable Embryogenic Callus", Bio/Technology, Jun. 1992, vol. 10, pp. 667-674.

Vasil V, al., "Regeneration of Plants From Embryogenic Suspension Culture Protoplasts of Wheat (*Triticum aestivum* L.)", Bio/Technology, May 1990, vol. 8, pp. 429-434.

Wosnick, et al., Gene, vol. 60, p. 115, (1987).

Wyrambik D, al., "Purification and Properties of Isoenzymes of Cinnamyl-Alcohol Dehydrogenase from Soybean-Cell-Suspension Cultures", European Journal of Biochemistry, Springer-Verlag, Nov. 1975, vol. 59, No. 1, pp. 9-15.

Yahiooui et al., "Comparative Efficiency of Different Constructs for Down Regulation of Tobacco Cinnamyl Alcohol Dehydrogenase", Phytochemistry, Elsevier Science Ltd., 1998, vol. 49, No. 2, pp. 295-306.

Aronen, "Genetic transformation of Scots pine (*Pinus sylvestris* L.)," *Dissertation Metsäntutkimuslaitoksen tiedonantoja*, 1996, vol. 595, pp. 8-53.

Asamizu et al., "Structural Analysis of *Arabidopsis thaliana* Chromosone 5,VIII. Sequence Features of the Regions of 1,081,958 bp Covered by Seventeen Physically assigned P1 and TAC Clones," *DNA Research*, 1998, vol. 5, pp. 379-391.

Baker et al., "The 5'-region of *Arabidopsis thaliana* cor15a has cis-acting elements that confer cold-, drought- and ABA-regulated gene expression," *Plant Molecular Biology*, 1994, vol. 24, pp. 701-713.

Baranowskij et al., "A novel DNA binding protein with homology to Myb oncoproteins containing only one repeat can function as a transcriptional activator," *The EMBO Journal*, 1994, vol. 13, No. 22, pp. 5383-5392.

Baumann et al., "The DNA Binding Site of the Dof Protein NtBBF1 is Essential for Tissue-Specific and Auxin-Regulated Expression of the rolB Oncogene in Plants," *The Plant Cell*, 1999, vol. 11, pp. 323-333.

Belknap et al., "The role of Ubiquitin in plant senescence and stress reponses," *Trends in Plant Science*, 1996, vol. 1, No. 10, pp. 331-335.

Benfey et al., Science, 1990, vol. 250, pp. 959-966.

Bevan, "Binary Agrobacterium vectors for plant transformation," *Nucleic Acids Research*, 1984, vol. 12, No. 22, pp. 8711-8721.

Bilang et al., "PEG-mediated direct gene transfer and electroporation," *Plant Molecular Biology Manual*, 1994, A1, pp. 1-16.

Bradford, "A Rapid and Sensitive Method for the Quantitation of Microgram Quantities of Protein Utilizing the Principle of Protein-Dye Binding," *Analytical Biolchemistry*, 1976, vol. 72, pp. 248-254.

Callis et al., "Ubiquitin extension proteins of *Arabidopsis thaliana*," *JBC*, Jul. 25, 1990, vol. 265, No. 21, pp. 12486-12493.

Campisi et al., "Generation of enhancer trap lines in *Arabidopsis* and characterization of expression patterns in the Inflorescence," *The Plant Journal*, 1999, vol. 17, No. 6, pp. 699-707.

Christensen et al., "Maize polyubiquitin genes: structure, thermal perturbation of expression and transcript splicing, and promoter activity following transfer to protoplasts by electroporation," *Plant Molecular Biology*, 1992, vol. 18, pp. 675-689.

Connors et al., "Cloning and characterization of promoters from American chestnut capable of directing reporter gene expression in transgenic *Arabidopsis* plants," *Plant Science*, 2002, vol. 163, No. 4, pp. 771-781.

Curie et al., "The activation process of *Arabidopsis thaliana* A1 gene encoding the translation elongation factor EF-1a is conserved among angiosperms," *Plant Molecular Biology*, 1992, vol. 18, pp. 1083-1089.

Dunstan et al., *In Vitro Embryogenesis in Plants*, "Somatic Embryogenesis in Woody Plants," (Chapter 12), 1995, pp. 471-538.

Ellis et al., *EMBO Journal*, 1987. vol. 1, No. 1, pp. 11-16.

EMBL Accession No. D10851 (ATHCDC2BG), 2000.

EMBL Accession No. D63396 (NTBY2A, TOBBYI2A), 1999.

EMBL Accession No. U12012 (PTU12012), 1996.

Forde et al., "Nuclear Factors Interact with Conserved A/T-Rich Elements Upstream of a Nodule-Enhanced Glutamine Synthetase Gene from French Bean," *The Plant Cell*, Sep. 1990, vol. 2, pp. 925-939.

GenBank Accession No. AA220869 (gi:1838898), 1997.
GenBank Accession No. AB016885, 2000.
GenBank Accession No. AF041463, 1998.
GenBank Accession No. AF075270, 1998.
GenBank Accession No. AF077743, 1998.
GenBank Accession No. AF139445, 1999.
GenBank Accession No. AJ012552 (VFA012552), 1998.
GenBank Accession No. L41658 (SCFPOLY), 1995.
GenBank Accession No. M55147 X51434.
GenBank Accession No. U53418 (GMU53418), 1997.
GenBank Accession No. U73588, 1996.
GenBank Accession No. U90350 (PRU90350), 1997.
GenBank Accession No. X53043 (LEEF1A), 1995.
GenBank Accession No. X74814 (TGOMTRN), 1994.
GenBank Accession No. Z14990 (ATUBC9), 1993.
GenPept Accession No. AAA68878, 1995.
GenPept Accession No. AAB21993, 1993.
GenPept Accession No. CAA10056, 1998.
GenPept Accession No. CAA63531, 1995.
GepPept Accession No. AAD56019 (AF181491_1), 1999.

Girod et al., "Homologs of the essential ubiquitin conjugating enzymes UBC1, 4 and 5 in yeast are encoded by a multigene family in *Arabidopsis thaliana*," *The Plant Journal*, 1993, vol. 3, No. 4, pp. 545-552.

Graham et al., "Expression Patterns of Vascular-Specific Promoters Rolc and SH in Transgenic Potatoes and Their Use in Engineering PLRV-Resistant Plants," *Plant Molecular Biology*, 1997, vol. 33, No. 4, pp. 729-735.

Grotewold et al., "The myb-Homologous P Gene Controls Phlobaphene Pigmentation in Maize Floral Organs by Directly Activating a Flavonoid Biosynthetic Gene Subset," *Cell Press*, 1994, vol. 76, pp. 543-553.

Imajuku et al., "Exon-intron organization of the *Arabidopsis thaliana* protein kinase genes CDC2a and CDC2b," *FEBS Letters*, 1992, vol. 304, No. 1, pp. 73-77.

Iwasaki et al., "Identification of a cis-regulatory region of a gene in *Arabidopsis thaliana* whose induction by dehydration is mediated by abscisic acid and requires protein synthesis," *Mol. Gen. Genet.*, 1995, vol. 247, pp. 391-398.

Kawasaki et al., "Specific Regulation of Gene Expression by Antisense Nucleic Acids: A Summary of Methodologies and Associated Problems," *Artifical Organs*, 1996, vol. 20(B), pp. 836-848.

Kim et al., "Monolignol radical-radical coupling networks in western red cedar and *Arabidopsis* and their evolutionary implications," *Phytochemistry, Pergamon Press*, 2002, vol. 61, No. 3, pp. 311-322.

Kim et al., "A 20 Nucleotide Upstream Element is Essential for the Nopaline Synthase (nos) Promoter Activity," *Plant Molecular Biology*, 1994, vol. 24, pp. 105-117.

Kumagai et al., "The Involvement of Protein Synthesis Elongation Factor 1a in the Organization of Microtubules on the Perinuclear Region during the Cell Cycle Transition from M Phase to G1 Phase in Tobacco BY-2 Cells," *Bot. Acta.*, 1995, vol. 108, pp. 467-473.

Kunkel, "Rapid and efficient site-specific mutagenesis without phenotypic selection " *Proc. Natl. Acad. Sci. USA*, 1985, vol. 82, pp. 488-492.

Lam et al., "Binding site requirements and differential representation of TGA factors in nuclear ASF-1 activity," *Nucleic Acids Research*, 1995, pp. 3778-3785, vol. 23, No. 18, pp. 3778-3785.

Lauvergeat et al., "The vascular expression pattern directed by the *Eucalyptus gunnii* cinnamyl alcohol dehydrogenase EgCAD2 promoter is conserved among woody and herbaceous plant species," *Plant Molecular Biology*, 2002, vol. 50, No. 3, pp. 497-509.

Li et al., An Auxin-Inducible Element in Soybean SAUR Promoters, *Plant Physiol.*, 1994, vol. 106, pp. 37-43.

Liaud et al., *Proc. Nat'l. Acad. Sci.*, 1990, vol. 87, No. 22, pp. 8918-8922.

McIntyre et al., "Strategies for the suppression of peroxidase gene expression in tobacco. I. Designing efficient ribozymes," *Transgenic Research*, 1996, vol. 5, pp. 257-262.

Meier et al., "Novel conserved sequence motifs in plant G-box binding proteins and implications for interactive domains," *Nucleic Acids Research*, 1994, vol. 22, No. 3, pp. 470-478.

Menkens et al., "Isolation and characterization of a fourth *Arabidopsis thaliana* G-box-binding factor, which has similarities to Fos oncoprotein," *Proc. Natl. Acad. Sci. USA*, 1994, vol. 91, pp. 2522-2526.

Merrifield, "Solid Phase Peptide Synthesis, I. The Synthesis of a Tetrapeptide," *Synthesis of a Tetrapeptide*, 1963, vol. 85, pp. 2149-2154.

Min et al., "Long-Distance Genome Walking Using the Long and Accurate Polymerase Chain Reaction," *BioTechniques*, 1998, vol. 24, pp. 398-400.

Napoli et al., "Introduction of a Chimeric Chalcone Synthase Gene into Petunia Results in Reversible Co-Suppression of Homologous Genes in trans," *The Plant Cell*, 1990, vol. 2, pp. 279-289.

Niebel et al., "Post-Transcriptional Cosuppression of β-1,3-Glucanase Genes Does Not Affect Accumulation of Transgene Nuclear mRNA," *The Plant Cell*, 1995, vol. 7, pp. 347-358.

Nordin et al., "Differential expression of two related, low-temperature-induced genes in *Arabidopsis thaliana* (L.) Heynh.," *Plant Molecular Biology*, 1993, vol. 21, pp. 641-653.

Pearson et al., "Improved tools for biological sequence comparison," *Proc. Natl. Acad. Sci. USA*, 1988, vol. 85 pp. 2444-2448.

Pearson, "[5] Rapid end Sensitive Sequence Comparison with FASTP and FASTA," *Methods in Enzymology*, 1990, vol. 183, pp. 63-98.

Poeydomenge et al., "A cDNA Encoding S-Adenosyl-L-Methionine: Carreic Acid 3-O-Methyltransferase from *Eucalyptus*," *Plant Physiology*, 1994, vol. 105, pp. 749-750.

Roberts et al., "Somatic Embryogenesis Of Spruce," *Synseeds*, 1993, Chapter 23, pp. 427-450.

Robinson-Benion et al., "[23] Antisense Techniques," *Methods in Enzymology*, 1995, vol. 254, pp. 363-375.

Rogers et al., "Definition and Functional Implications of Gibberellin and Abscisic Acid cis-Acting Hormone Response Complexes," *The Plant Cell*, 1992, vol. 4, pp. 1443-1451.

Scharf et al,. "Heat Stress Promoters and Transcription Factors," *Results Probl Cell Differ*, 1994, vol. 20, pp. 125-162.

Shen et al., "Protein complexes binding to cis elements of the plant histone gene promoters: multiplicity, phosphorylation and cell cycle alteration," *Plant Molecular Biology*, 1997, vol. 33, pp. 367-379.

Swiss-Prot Accession No. O24493 (MC1 PINRA), 1999.

Szczyglowski et al., *The Plant Cell*, 1994, vol. 6, pp. 317-332.

Tenhaken et al., "Cloning of an Enzyme that Synthesizes a Key Nucleotide-Sugar Precursor of Hemicellulose Biosynthesis from Soybean: UDP-Glucose Dehydroegnase," *Plant Physiology*, 1996, vol. 112, pp. 1127-1134.

Ulmasov et al., "ARF1, a Transcription Factor That Binds to Auxin Response Elements," *Science*, 1997, vol. 276, pp. 1885-1858.

Valvekens et al., "Agrobacterium tumefaciens-medicated transformation of *Arabidopsis thaliana* root explants by using kanamycin selection," *Proc. Natl. Acad. Sci. USA*, 1988, vol. 85, pp. 5536-5540.

Vicente-Carbajosa et al., "A maize zinc-finger protein binds the prolamin box in zein gene promoters and interacts with the basic leucine zipper transcriptional activator Opaque2," *Proc. Natl. Acad. Sci. USA*, 1997, vol. 94, pp. 7685-7690.

Voo et al., "4-Coumarate:Coenzyme A Ligase from Lobiolly Pine Xylem. Isolation, Characterization, and Complementary DNA Cloning," *Plant Physiology*, 1995, vol. 108, pp. 85-97.

Walden et al., "Genes expressed in *Pinus radiate* Male Cones Include Homologs to Anther-Specific and Pathogenesis Response Genes," *Plant Physiology*, 1999, vol. 121, pp. 1103-1116.

The PTO form PTO-892, from the related U.S. Appl. No. 12/205,329, dated Mar. 23, 2011.

Buzeli R.A., et. al., "Tissue-specific regulation of BiP genes: a cis-acting regulatory domain is required for BiP promoter activity in plant meristems", *Plant Mol Biol.*, Nov. 2002; 50(4-5), pp. 757-771.

Gillespie D., "The magic and challenge of DNA probes as diagnostic reagents", *Vet Microbiol.*, Sep. 1990; 24(3-4), pp. 217-233. Review.

Kim Y., et al., "A 20 nucleotide upstream element is essentialf or the nopaline synthase (nos) promoter activity", *Plant Mol Biol.*, Jan. 1994; 24(1), pp. 105-117.

* cited by examiner

Figure 1: Nucleic Acid Sequence of 534 bp COMT Promoter (SEQ ID NO: 1)

ATGCGCCATGTTGACAAAAAGGCTGATTAGTATGATCTTGGAGTTGTTGGTGCAA
ATTTGCAAGCTGACGATGGCCCCTCAGGGAAATTAAGGCGCCAACCCAGATTGC
AAAGAGCACAAAGAGCACGACCCAACCTTTCCTTAACAAGATCATCACCAGATC
GGCCAGTAAGGGTAATATTAATTTAACAAATAGCTCTTGTACCGGGAACTCCGTA
TTTCTCTCACTTCCATAAACCCCTGATTAATTTGGTGGGAAAGCGACAGCCAACC
CACAAAAGGTCAGATGTCATCCCACGAGAGAGAGAGAGAGAGAGAGAGAGAGA
GAGTTTTCTCTCTATATTCTGGTTCACCGGTTGGAGTCAATGGCATGCGTGACGAA
TGTACATATTGGTGTAGGGTCCAATATTTTGCGGGAGGGTTGGTGAACCGCAAAG
TTCCTATATATCGAACCTCCACCACCATACCTCACTTCAATCCCCACCATTTATCC
GTTTTATTTCCTCTGCTTTCCTTTGCTCGAGTCTCGCGGAA

Figure 2: Nucleic Acid Sequence of 485 bp COMT Promoter (SEQ ID NO: 2)

GTGCAAATTTGCAAGCTGACGATGGCCCCTCAGGGAAATTAAGGCGCCAACCCA
GATTGCAAAGAGCACAAAGAGCACGACCCAACCTTTCCTTAACAAGATCATCAC
CAGATCGGCCAGTAAGGGTAATATTAATTTAACAAATAGCTCTTGTACCGGGAAC
TCCGTATTTCTCTCACTTCCATAAACCCCTGATTAATTTGGTGGGAAAGCGACAGC
CAACCCACAAAAGGTCAGATGTCATCCCACGAGAGAGAGAGAGAGAGAGAGAG
AGAGAGAGTTTTCTCTCTATATTCTGGTTCACCGGTTGGAGTCAATGGCATGCGT
GACGAATGTACATATTGGTGTAGGGTCCAATATTTTGCGGGAGGGTTGGTGAACC
GCAAAGTTCCTATATATCGAACCTCCACCACCATACCTCACTTCAATCCCCACCAT
TTATCCGTTTTATTTCCTCTGCTTTCCTTTGCTCGAGTCTCGCGGAA

Figure 3: Nucleic Acid Sequence of 306 bp COMT Promoter (SEQ ID NO: 3)

TTCCATAAACCCCTGATTAATTTGGTGGGAAAGCGACAGCCAACCCACAAAAGGT
CAGATGTCATCCCACGAGAGAGAGAGAGAGAGAGAGAGAGAGAGTTTTCTCT
CTATATTCTGGTTCACCGGTTGGAGTCAATGGCATGCGTGACGAATGTACATATT
GGTGTAGGGTCCAATATTTTGCGGGAGGGTTGGTGAACCGCAAAGTTCCTATATA
TCGAACCTCCACCACCATACCTCACTTCAATCCCCACCATTTATCCGTTTTATTTC
CTCTGCTTTCCTTTGCTCGAGTCTCGCGGAA

Figure 4: Nucleic Acid Sequence of 293 bp COMT Promoter (SEQ ID NO: 4)

TGATTAATTTGGTGGGAAAGCGACAGCCAACCCACAAAAGGTCAGATGTCATCC
CACGAGAGAGAGAGAGAGAGAGAGAGAGAGAGTTTTCTCTCTATATTCTGGT
TCACCGGTTGGAGTCAATGGCATGCGTGACGAATGTACATATTGGTGTAGGGTCC
AATATTTTGCGGGAGGGTTGGTGAACCGCAAAGTTCCTATATATCGAACCTCCAC
CACCATACCTCACTTCAATCCCCACCATTTATCCGTTTTATTTCCTCTGCTTTCCTT
TGCTCGAGTCTCGCGGAA

Figure 5: Nucleic Acid Sequence of 119 bp COMT Promoter (SEQ ID NO: 5)

GGAGGGTTGGTGAACCGCAAAGTTCCTATATATCGAACCTCCACCACCATACCTC
ACTTCAATCCCCACCATTTATCCGTTTTATTTCCTCTGCTTTCCTTTGCTCGAGTCT
CGCGGAA

Figure 6: Nucleic Acid Sequence of 99 bp COMT Promoter (SEQ ID NO: 6)

AGTTCCTATATATCGAACCTCCACCACCATACCTCACTTCAATCCCCACCATTTAT
CCGTTTTATTTCCTCTGCTTTCCTTTGCTCGAGTCTCGCGGA

Figure 7: Nucleic Acid Sequence of 66 bp COMT Promoter (SEQ ID NO: 7)

TCACTTCAATCCCCACCATTTATCCGTTTTATTTCCTCTGCTTTCCTTTGCTCGAGT
CTCGCGGAA

Reporter activity of the COMT promoter fused to *uidA* in medium without plant growth regulator (FK) or with NAA or BA

SEQUENCE LISTING

<160> NUMBER OF SEQ ID NOS: 8

<210> SEQ ID NO 1
<211> LENGTH: 534
<212> TYPE: DNA
<213> ORGANISM: Eucalyptus grandis

<400> SEQUENCE: 1

```
atgcgccatg ttgacaaaaa ggctgattag tatgatcttg gagttgttgg tgcaaatttg      60
caagctgacg atggcccctc agggaaatta aggcgccaac ccagattgca aagagcacaa     120
agagcacgac ccaacctttc cttaacaaga tcatcaccag atcggccagt aagggtaata     180
ttaatttaac aaatagctct tgtaccggga actccgtatt tctctcactt ccataaaccc     240
ctgattaatt tggtgggaaa gcgacagcca acccacaaaa ggtcagatgt catcccacga     300
gagagagaga gagagagaga gagagagagt tttctctcta tattctggtt caccggttgg     360
agtcaatggc atgcgtgacg aatgtacata ttggtgtagg gtccaatatt ttgcgggagg     420
gttggtgaac cgcaaagttc ctatatatcg aacctccacc accatacctc acttcaatcc     480
ccaccattta tccgttttat ttcctctgct ttcctttgct cgagtctcgc ggaa           534
```

<210> SEQ ID NO 2
<211> LENGTH: 485
<212> TYPE: DNA
<213> ORGANISM: Eucalyptus grandis

<400> SEQUENCE: 2

```
gtgcaaattt gcaagctgac gatggcccct cagggaaatt aaggcgccaa cccagattgc      60
aaagagcaca aagagcacga cccaaccttt ccttaacaag atcatcacca gatcggccag     120
taagggtaat attaatttaa caaatagctc ttgtaccggg aactccgtat tctctcact      180 tccataaacc cctgattaat ttggtgggaa agcgacagcc aacccacaaa aggtcagatg     240
tcatcccacg agagagagag agagagagag agagagagag ttttctctct atattctggt     300
tcaccggttg gagtcaatgg catgcgtgac gaatgtacat attggtgtag gtccaatat      360 tttgcgggag ggttggtgaa ccgcaaagtt cctatatatc gaacctccac caccatacct     420
cacttcaatc cccaccattt atccgtttta tttcctctgc tttcctttgc tcgagtctcg     480
cggaa                                                                 485
```

<210> SEQ ID NO 3
<211> LENGTH: 306
<212> TYPE: DNA
<213> ORGANISM: Eucalyptus grandis

<400> SEQUENCE: 3

```
ttccataaac ccctgattaa tttggtggga aagcgacagc caacccacaa aaggtcagat      60
gtcatcccac gagagagaga gagagagaga gagagagaga gttttctctc tatattctgg     120
ttcaccggtt ggagtcaatg gcatgcgtga cgaatgtaca tattggtgta gggtccaata     180
ttttgcggga gggttggtga accgcaaagt tcctatatat cgaacctcca ccaccatacc     240
tcacttcaat ccccaccatt tatccgtttt atttcctctg ctttcctttg ctcgagtctc     300
gcggaa                                                                306
```

```
<210> SEQ ID NO 4
<211> LENGTH: 293
<212> TYPE: DNA
<213> ORGANISM: Eucalyptus grandis

<400> SEQUENCE: 4
tgattaattt ggtgggaaag cgacagccaa cccacaaaag gtcagatgtc atcccacgag      60
agagagagag agagagagag agagagagtt ttctctctat attctggttc accggttgga     120
gtcaatggca tgcgtgacga atgtacatat tggtgtaggg tccaatattt tgcgggaggg     180
ttggtgaacc gcaaagttcc tatatatcga acctccacca ccatacctca cttcaatccc     240
caccatttat ccgtttattt tcctctgctt tcctttgctc gagtctcgcg gaa            293

<210> SEQ ID NO 5
<211> LENGTH: 119
<212> TYPE: DNA
<213> ORGANISM: Eucalyptus grandis

<400> SEQUENCE: 5
ggagggttgg tgaaccgcaa agttcctata tatcgaacct ccaccaccat acctcacttc      60 aatcccacc atttatccgt tttatttcct ctgctttcct tgctcgagt ctcgcggaa        119

<210> SEQ ID NO 6
<211> LENGTH: 98
<212> TYPE: DNA
<213> ORGANISM: Eucalyptus grandis

<400> SEQUENCE: 6
agttcctata tatcgaacct ccaccaccat acctcacttc aatcccacc atttatccgt      60 tttatttcct ctgctttcct tgctcgagt ctcgcgga                              98

<210> SEQ ID NO 7
<211> LENGTH: 66
<212> TYPE: DNA
<213> ORGANISM: Eucalyptus grandis

<400> SEQUENCE: 7
tcacttcaat ccccaccatt tatccgtttt atttcctctg ctttcctttg ctcgagtctc      60
gcggaa                                                                66

<210> SEQ ID NO 8
<211> LENGTH: 11
<212> TYPE: DNA
<213> ORGANISM: Eucalyptus grandis

<400> SEQUENCE: 8
ccataaaccc c                                                          11
```

VASCULAR-PREFERRED PROMOTER SEQUENCES AND USES THEREOF

CROSS-REFERENCE TO RELATED APPLICATION

This application is a divisional of U.S. application Ser. No. 10/703,091, filed Nov. 7, 2003, now allowed, which claims priority to U.S. Provisional Application No. 60/428,287, filed Nov. 22, 2002.

FIELD OF INVENTION

The present invention relates to the regulation of polynucleotide transcription and/or expression. In particular, this invention relates to polynucleotide regulatory sequences isolated from *Eucalyptus grandis* that are capable of initiating and promoting the transcription of polynucleotides in plant cells undergoing xylogenesis. Constructs and methods for using the inventive regulatory sequences for modifying transcription of endogenous and/or heterologous polynucleotides also are included in the invention.

BACKGROUND OF THE INVENTION

Lignin is one of the major products of the phenylpropanoid pathway, and is one of the most abundant organic molecules in the biosphere (Crawford, (1981) Lignin Biodegradation and Transformation, New York: John Wiley and Sons). During lignin biosynthesis, caffeic acid is believed to be O-methylated by caffeic acid/5-hydroxyferulic acid O-methyltransferase (COMT) to form ferulic acid, a direct precursor of lignin. COMT is also believed to play a role in the final hydroxylation reaction of the general phenylpropanoid pathway, in which it O-methylates 5-hydroxyferulate. This dual specificity of COMT has been confirmed by the cloning of the COMT gene, and expression of the protein in *E. coli* (Bugos et al., *Plant Mol. Biol.* 17, 1203, (1991); Gowri et al., (1991) *Plant Physiol.*, 97, 7, (1991)). The expression pattern of the COMT gene and the evidence from mutations of the COMT gene are consistent with this role in lignification (Marita et al., J. Chem. Soc., Perkin Trans. 1, 2939-2945 (2001). Accordingly, COMT is believed to play an important role in lignin biosynthesis, and control of COMT expression may provide a means for regulating lignin biosynthesis and other processes that occur concurrently in cell wall development, such as formation of hemicellulose and lignocellulosic polymers.

Lignin biosynthesis can be regulated at the level of transcription. During transcription, a single-stranded RNA complementary to the DNA sequence to be transcribed is formed by the action of RNA polymerases. Initiation of transcription in eucaryotic cells is regulated by complex interactions between cis-acting DNA motifs, located upstream of the gene to be transcribed, and trans-acting protein factors. Among the cis-acting regulatory elements are sequences of DNA, termed promoters, which are located close to the transcription initiation site and to which RNA polymerase is first bound, either directly or indirectly. Promoters usually consist of proximal (e.g. TATA box) and more distant elements (e.g. CCAAT box). Enhancers are cis-acting DNA motifs which may be situated 5-prime and/or 3-prime from the initiation site.

Both promoters and enhancers are generally composed of several discrete, often redundant, elements each of which may be recognized by one or more trans-acting regulatory proteins, known as transcription factors. Regulation of the complex patterns of gene expression observed both spatially and temporally, in all developing organisms, is thought to arise from the interaction of enhancer- and promoter-bound, general and tissue-preferred transcription factors with DNA (Izawa T, Foster R and Chua N H, 1993, *J. Mol. Biol.* 230: 1131-1144; Menkens A E, Schindler U and Cashmore A R, 1995, *Trends in Biochem Sci* 13:506-510).

Genetic regulation of biochemical pathways may be conducted in narrowly restricted tissue types to avoid global, detrimental effects to the modified plants. For example, when the content or composition of lignin is affected by expression of a particular gene product, it may be desirable to limit the expression of the gene product to certain segments of the plant or to certain developmental stages, to avoid decreasing the plant's disease resistance. A heterologous gene may be expressed in a selected tissue by operably linking it to a tissue-preferred promoter. Suitable tissue-preferred promoters include the bean grp1.8 promoter, which is specifically active in protoxylem tracheary elements of vascular tissue. Keller et al., *EMBO J.* 8: 1309 (1989). These promoters also include the *Eucalyptus* CAD promoter, which is preferentially expressed in lignifying zones. Feuillet et al., *Plant Mol. Biol.* 27: 651 (1995). Such tissue-preferred promoters have been used to regulate gene expression of antisense molecules in specific tissues. Van der Meer et al., *Plant Cell* 4: 253 (1992), Salehuzzaman et al., *Plant Mol. Biol.* 23: 947 (1993), and Matsuda et al., *Plant Cell Physiol.* 37: 215 (1996).

Because tissue-preferred promoters may be less active in a heterologous environment, they do not always express genes to the same levels achieved with constitutive promoters. Yahiaoui et al., *Phytochemistry* 49: 295-306 (1998). Further, the developmental window during which these promoters are active, or the spatial distribution of their activity, may limit their usefulness. Thus, there is a continuing need in the art for additional tissue-preferred promoters, especially vascular-preferred promoter sequences, that have desirable spatial and temporal patterns of expression. Grima-Pettenati et al., *Plant Science* 145: 51-65 (1999).

WO 01/98485 and U.S. Ser. No. 10/137,036 disclose a full-length *Eucalyptus grandis* COMT promoter and 661 base pair fragment. However, neither application suggests that other deletion fragments of the *Eucalyptus grandis* COMT promoter are active as promoters in and of themselves, or that such deletion fragments might confer tissue-preferred, tissue-specific, or vascular-preferred expression.

SUMMARY OF THE INVENTION

The present invention relates to isolated polynucleotide regulatory sequences of the *Eucalyptus grandis* COMT promoter that confer vascular-preferred gene expression In one aspect, the present invention provides an isolated polynucleotide selected from any one of SEQ ID NO: 1 to 7 and functional variants thereof.

In one embodiment, the isolated polynucleotide confers vascular-preferred gene expression in a plant cell.

In another embodiment, the isolated polynucleotide confers xylem-preferred gene expression in a plant cell.

In a further embodiment, a functional variant has a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% in sequence to any one of SEQ ID NO: 1 to 7.

In another aspect, the invention provides an isolated polynucleotide having a sequence selected from (i) sequences that are complementary to a isolated polynucleotide selected from any one of SEQ ID NO: 1 to 7 and functional variants thereof, (ii) sequences that are reverse sequences of a isolated polynucleotide selected from any one of SEQ ID NO: 1 to 7 and functional variants thereof, and (iii) sequences that are reverse complements of a isolated polynucleotide selected from any one of SEQ ID NO: 1 to 7 and functional variants thereof.

In one embodiment, an isolated polynucleotide is provided that hybridizes under stringent conditions to a isolated polynucleotide selected any one of SEQ ID NO: 1 to 7 and functional variants thereof, wherein said isolated polynucleotide hybridizes over its full-length sequence to any one of SEQ ID NO: 1 to 7 and functional variants thereof.

In another embodiment, the isolated polynucleotide is capable of at least one of (i) binding to a nucleic acid molecule or (ii) regulating expression of an operably-linked gene in a monocotyledonous plant.

In another embodiment, the isolated polynucleotide is capable of at least one of (i) binding to a nucleic acid molecule or (ii) regulating expression of an operably-linked gene in a dicotyledonous plant.

In another embodiment, the isolated polynucleotide is capable of upregulating or downregulating the expression of an operably-linked gene in a plant.

In another aspect, the invention provides a DNA construct comprising an isolated polynucleotide selected from any one of SEQ ID NO: 1 to 7 and functional variants thereof operably linked to a desired nucleic acid, wherein the promoter regulates the expression of the desired nucleic acid.

In one embodiment, the polynucleotide upregulates or down-regulates expression of the desired nucleic acid.

In another embodiment, the desired nucleic acid encodes an enzyme in the lignin biosynthetic pathway.

In another embodiment, the desired nucleic acid produces an RNA transcript.

In a further embodiment, the RNA transcript has an antisense sequence of a gene that is endogenous to a plant cell.

In a yet another embodiment, the RNA transcript induces RNA interference of a gene that is normally expressed in a plant cell.

In another aspect, the invention contemplates a plant transformed with a DNA construct comprising an isolated polynucleotide selected from any one of SEQ ID NO: 1 to 7 and functional variants thereof operably linked to a desired nucleic acid, wherein the promoter regulates the expression of the desired nucleic acid.

In one embodiment, the phenotype of a plant transformed with the inventive DNA construct expresses a difference in lignin quality compared with a plant of the same species that is not transformed with the DNA construct. In a further embodiment, the difference in lignin quality is characterized by change in the structure of the lignin molecule.

In another embodiment, the phenotype of a plant transformed with the inventive DNA construct expresses a difference in wood composition compared to a plant of the same species that is not transformed with said DNA construct.

In another aspect, the invention contemplates a plant cell comprising a DNA construct comprising (i) a polynucleotide having the sequence of any one of SEQ ID NO: 1 to 7 and functional variants thereof and (ii) a desired nucleic acid, wherein said polynucleotide is operably linked to the desired nucleic acid.

In one embodiment, a transgenic plant comprises a plant cell comprising a DNA construct comprising (i) a polynucleotide having the sequence of any one of SEQ ID NO: 1 to 7 and functional variants thereof and (ii) a desired nucleic acid, wherein said polynucleotide is operably linked to the desired nucleic acid.

In another aspect, the invention provides a method for producing a transgenic plant, comprising (a) transforming a plant cell with a DNA construct that comprises (i) at least one polynucleotide having the sequence of any one of SEQ ID NOs. 1 to 7 or functional variants thereof and (ii) a desired nucleic acid, wherein the polynucleotide regulates the activity of the desired sequence; (b) culturing the transformed plant cell under conditions that promote growth of a plant, wherein the plant is a transgenic plant that exhibits a phenotype that is different from a plant of the same species that does not contain said DNA construct.

In one embodiment, the phenotype of the transformed plant is characterized by a difference in lignin quality compared to a plant of the same species that does not contain the DNA construct.

In another embodiment, the phenotype of the transformed plant is characterized by a difference in fiber yield compared to a plant of the same species that does not contain the DNA construct.

In another embodiment, the phenotype of the transformed plant is characterized by a difference in plant cell development compared to a plant of the same species that does not contain the DNA construct.

In another aspect, the invention provides a method for reducing lignin in a plant, comprising (a) introducing into a plant cell a DNA construct comprising (i) a promoter having the sequence of any one of SEQ ID NOs: 1 to 7 or functional variants thereof and (ii) a nucleic acid encoding a gene involved in lignin biosynthesis, wherein the nucleic acid is antisense relative to the promoter and wherein the promoter regulates the expression of the gene; (b) culturing the transformed plant cell under conditions that promote growth of a plant, wherein the plant is a transgenic plant that exhibits a phenotype that is different from a plant of the same species that does not contain the DNA construct; and (c) selecting a plant having reduced lignin content.

In another aspect, the present invention provides a method for increasing lignin in a plant, comprising (a) introducing into a plant cell a DNA construct comprising (i) a promoter having the sequence of any one of SEQ ID NOs: 1 to 7 or functional variants thereof and (ii) a nucleic acid encoding a gene involved in lignin biosynthesis, wherein the promoter regulates the expression of the gene; (b) culturing the transformed plant cell under conditions that promote growth of a plant, wherein the plant is a transgenic plant that exhibits a phenotype that is different from a plant of the same species that does not contain the DNA construct; and (c) selecting a plant having increased lignin content.

In yet another aspect, the present invention provides a method for obtaining wood, comprising (a) introducing into a plant cell of a woody plant a DNA construct comprising (i) a promoter having the sequence of any one of SEQ ID NOs: 1 to 7 or functional variants thereof and (ii) and a desired nucleic acid, wherein the promoter regulates the expression of the desired nucleic acid; (b) culturing the transformed plant cell under conditions that promote growth of a plant; and (c) obtaining wood from the plant.

In one embodiment, the woody plant is selected from a species of *Eucalyptus* or *Pinus*.

In another aspect, the invention provides a method for obtaining wood pulp, comprising (a) introducing into a plant cell of a woody plant a DNA construct comprising (i) a promoter having the sequence of any one of SEQ ID NOs: 1 to 7 or functional variants thereof and (ii) and a desired nucleic acid, wherein the promoter regulates the expression of the desired nucleic acid; (b) culturing the transformed plant cell under conditions that promote growth of a plant; and (c) obtaining wood pulp from the plant.

In one embodiment, the woody plant is selected from a species of *Eucalyptus* or *Pinus*.

BRIEF DESCRIPTION OF THE DRAWINGS

FIG. 1 depicts the nucleic acid sequence of 534 bp COMT promoter (SEQ ID NO: 1).

FIG. 2 depicts the nucleic acid sequence of 485 bp COMT promoter (SEQ ID NO: 2).

FIG. 3 depicts the nucleic acid sequence of 306 bp COMT promoter (SEQ ID NO: 3).

FIG. 4 depicts the nucleic acid sequence of 293 bp COMT promoter (SEQ ID NO: 4).

FIG. 5 depicts the nucleic acid sequence of 119 bp COMT promoter (SEQ ID NO: 5).

FIG. 6 depicts the nucleic acid sequence of 99 bp COMT promoter (SEQ ID NO: 6).

FIG. 7 depicts the nucleic acid sequence of 66 bp COMT promoter (SEQ ID NO: 7).

DETAILED DESCRIPTION OF THE PREFERRED EMBODIMENTS

Figure 8:
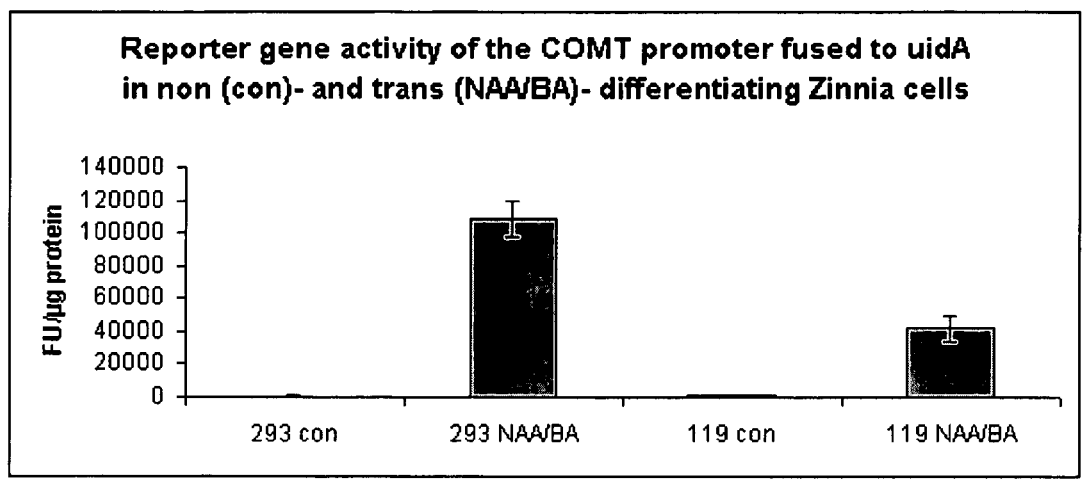
FIG. 8 displays COMT promoter deletion analyses.

While it is known that the *E. grandis* COMT promoter drives gene expression in developing xylem cells, little is known about how this promoter initiates transcription. Bioinformatic analysis of the COMT promoter reveals no previously known cis elements. However, the present inventors identified putative vascular specific factor-like and AC rich-like elements that vary from sequences published in, e.g., Kawaoka et al., 2000; Lacombe et al., 2000, and Ringli and Keller, 1998. Based on the presence of these putative regulatory elements, a series of deletion fragments of the COMT promoter were designed and constructed in accordance with the present invention. Thus, in one aspect, the present invention relates to isolated regulatory sequences of the COMT promoter. These regulatory sequences confer vascular-preferred gene expression and can be used to transform plants.

The present invention therefore relates to isolated polynucleotide regulatory sequences of the *Eucalyptus grandis* COMT promoter that confer vascular-preferred gene expression. Transformation of a plant with an inventive polynucleotide sequence permits regulation of plant gene expression. The polynucleotide sequences of the present invention can be employed to modify properties such as cellulose synthesis, lignin deposition, other aspects of wood development, flower development, root development, branching, seasonal responses such as light and cold controls on meristem identity, and disease resistance. The present invention also provides a DNA construct comprising an inventive polynucleotide regulatory sequence operably linked to a second polynucleotide sequence, wherein the inventive polynucleotide sequence regulates transcription of the second polynucleotide sequence. Additionally, the invention provides methods for assaying the activity of an inventive polynucleotide sequence, and methods for using inventive polynucleotide sequences for modifying growth, wood development and/or fiber composition in a plant.

The present invention uses terms and phrases that are well known to those practicing the art. Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described herein are those well known and commonly employed in the art. Standard techniques are used for recombinant nucleic acid methods, polynucleotide synthesis, microbial culture, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. The techniques and procedures are generally performed according to conventional methodology. See, e.g., Sambrook & Russel, MOLECULAR CLONING: A LABORATORY MANUAL, $3^{rd}$ ed., Cold Spring Harbor Laboratory Press, Cold Spring Harbor, N.Y., 2001.

*Agrobacterium*: as is well known in the field, *Agrobacteria* that are used for transforming plant cells are disarmed and virulent derivatives of, usually, *Agrobacterium tumefaciens* or *Agrobacterium rhizogenes* that contain a vector. The vector typically contains a desired polynucleotide that is located between the borders of a T-DNA.

Angiosperm: vascular plants having seeds enclosed in an ovary. Angiosperms are seed plants that produce flowers that bear fruits. Angiosperms are divided into dicotyledonous and monocotyledonous plants.

Desired Polynucleotide: a desired polynucleotide of the present invention is a genetic element, such as a promoter, enhancer, or terminator, or gene or polynucleotide that is to be transcribed and/or translated in a transformed cell that comprises the desired polynucleotide in its genome. If the desired polynucleotide comprises a sequence encoding a protein product, the coding region may be operably linked to regulatory elements, such as to a promoter and a terminator, that bring about expression of an associated messenger RNA transcript and/or a protein product encoded by the desired polynucleotide. Thus, a "desired polynucleotide" may comprise a gene that is operably linked in the 5'- to 3'-orientation, a promoter, a gene that encodes a protein, and a terminator. Alternatively, the desired polynucleotide may comprise a gene or fragment thereof in an "antisense" orientation, the transcription of which produces nucleic acids that may form secondary structures that affect expression of an endogenous gene in the plant cell. A desired polynucleotide may also yield a double-stranded RNA product upon transcription that initiates RNA interference of a gene to which the desired polynucleotide is associated. A desired polynucleotide of the present invention may be positioned within a T-DNA, such that the left and right T-DNA border sequences flank or are on either side of the desired polynucleotide. The present invention envisions the stable integration of one or more desired polynucleotides into the genome of at least one plant cell. A desired polynucleotide may be mutated or may be a variant of its wild-type sequence. It is understood that all or part of the desired polynucleotide can be integrated into the genome of a plant. It also is understood that the term "desired polynucleotide" encompasses one or more of such polynucleotides. Thus, a T-DNA of the present invention may comprise one, two, three, four, five, six, seven, eight, nine, ten, or more desired polynucleotides.

Dicotyledonous plant (dicot): a flowering plant whose embryos have two seed halves or cotyledons, branching leaf veins, and flower parts in multiples of four or five. Examples of dicots include but are not limited to, *Eucalyptus, Populus, Liquidamber, Acacia*, teak, mahogany, cotton, tobacco, *Arabidopsis*, tomato, potato sugar beet, broccoli, cassava, sweet potato, pepper, poinsettia, bean, alfalfa, soybean, carrot, strawberry, lettuce, oak, maple, walnut, rose, mint, squash, daisy, geranium, avocado, and cactus.

Endogenous refers to a gene that is native to a plant genome.

Fiber composition: as used herein, fiber composition refers to a trait that can be modified to change the structure, appearance, or use of fiber. Traits that determine fiber composition include but are not limited to fiber length, coarseness, strength, color, cross-sectional, width, and fiber density. For example, it is known that fiber length imparts strength, whereas fiber coarseness determines texture and flexibility.

Foreign: "foreign," with respect to a nucleic acid, means that that nucleic acid is derived from non-plant organisms, or derived from a plant that is not the same species as the plant to be transformed or is not derived from a plant that is not interfertile with the plant to be transformed, or does not belong to the species of the target plant. According to the present invention, foreign DNA or RNA may include nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product.

Gene: A gene is a segment of a DNA molecule that contains all the information required for synthesis of a product, polypeptide chain or RNA molecule, and includes both coding and non-coding sequences.

Genetic element: a "genetic element" is any discreet nucleotide sequence including, but not limited to, a promoter, a gene, a terminator, an intron, an enhancer, a spacer, a 5'-untranslated region, a 3'-untranslated region, or a recombinase recognition site.

Genetic modification: stable introduction of DNA into the genome of certain organisms by applying methods in molecular and cell biology.

Gymnosperm: as used herein, refers to a seed plant that bears seed without ovaries. Examples of gymnosperms include conifers, cycads, ginkgos, and ephedras.

Introduction: as used herein, refers to the insertion of a nucleic acid sequence into a cell, by methods including infection, transfection, transformation or transduction.

Juvenility: describes a physiological difference between a young tree and a mature tree. In the present invention, juvenility refers to differences in microfibril angle, wood density, cellulose yield, regenerability, and reproductive ability between a young tree and a mature tree. For example, it has been shown that as a woody plant tissue matures, the tissue loses its ability to regenerate.

Lignin: as used herein, refers to a polymeric composition composed of phenylpropanoid units, including polymerized derivatives of monolignols coniferyl, coumaryl, and sinapyl alcohol. Lignin quality refers to the ability of a lignin composition to impart strength to cell wall matrices, assist in the transport of water, and/or impede degradation of cell wall polysaccharides. Lignin composition or lignin structure may be changed by altering the relative amounts of each of monolignols or by altering the type of lignin. For example, guaiacyl lignins (derived from ferulic acid) are prominent in softwood species, whereas guaiacyl-syringyl lignins (derived from ferulic acid and sinapic acid) are characteristic of hardwood species. The degradation of lignin from softwoods, such as pine, requires substantially more alkali and longer incubations, compared with the removal of lignin from hardwoods. Lignin composition may be regulated by either up-regulation or down-regulation of enzymes involved lignin biosynthesis. For example, key lignin biosynthsesis enzymes include, but are not limited to, 4-coumaric acid: coenzyme A ligase (4CL), Cinnamyl Alcohol dehydrogenase (CAD), and Sinapyl Alcohol Dehydrogenase (SAD).

Monocotyledonous plant (monocot): a flowering plant having embryos with one cotyledon or seed leaf, parallel leaf veins, and flower parts in multiples of three. Examples of monocots include, but are not limited to turfgrass, maize, rice, oat, wheat, barley, sorghum, orchid, iris, lily, onion, and palm. Examples of turfgrass include, but are not limited to *Agrostis* spp. (bentgrass species including colonial bentgrass and creeping bentgrasses), *Poa pratensis* (kentucky bluegrass), *Lolium* spp. (ryegrass species including annual ryegrass and perennial ryegrass), *Festuca arundinacea* (tall fescue) *Festuca rubra commutata* (fine fescue), *Cynodon dactylon* (common bermudagrass varieties including Tifgreen, Tifway II, and Santa Ana, as well as hybrids thereof); *Pennisetum clandestinum* (kikuyugrass), *Stenotaphrum secundatum* (st. augustinegrass), *Zoysia japonica* (zoysiagrass), and *Dichondra micrantha*.

Operably linked: combining two or more molecules in such a fashion that in combination they function properly in a plant cell. For instance, a promoter is operably linked to a structural gene when the promoter controls transcription of the structural gene.

Phenotype: phenotype is a distinguishing feature or characteristic of a plant, which may be altered according to the present invention by integrating one or more "desired polynucleotides" and/or screenable/selectable markers into the genome of at least one plant cell of a transformed plant. The "desired polynucleotide(s)" and/or markers may confer a change in the phenotype of a transformed plant by modifying any one of a number of genetic, molecular, biochemical, physiological, morphological, or agronomic characteristics or properties of the transformed plant cell or plant as a whole. Thus, expression of one or more, stably integrated desired polynucleotide(s) in a plant genome may yield a phenotype selected from the group consisting of, for example, increased drought tolerance, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved vigor, improved taste, improved texture, decreased phosphate content, increased germination, increased micronutrient uptake, improved starch composition, and improved flower longevity.

Plant tissue: a "plant" is any of various photosynthetic, eukaryotic, multicellular organisms of the kingdom Plantae characteristically producing embryos, containing chloroplasts, and having cellulose cell walls. A part of a plant, i.e., a "plant tissue" may be transformed according to the methods of the present invention to produce a transgenic plant. Many suitable plant tissues can be transformed according to the present invention and include, but are not limited to, somatic embryos, pollen, leaves, stems, calli, stolons, microtubers, and shoots. Thus, the present invention envisions the transformation of angiosperm and gymnosperm plants such as turfgrass, wheat, maize, rice, barley, oat, sugar beet, potato, tomato, tobacco, alfalfa, lettuce, carrot, strawberry, cassava, sweet potato, geranium, soybean, oak, apple, grape, pine, fir, acacia, eucalyptus, walnut, and palm. According to the present invention "plant tissue" also encompasses plant cells. Plant cells include suspension cultures, callus, embryos, meristematic regions, callus tissue, leaves, roots, shoots, gametophytes, sporophytes, pollen, seeds and microspores. Plant tissues may be at various stages of maturity and may be grown in liquid or solid culture, or in soil or suitable media in pots, greenhouses or fields. A plant tissue also refers to any clone of such a plant, seed, progeny, propagule whether generated sexually or asexually, and descendents of any of these, such as cuttings or seed. Of particular interest are conifers such as pine, fir and spruce, monocots such as Kentucky bluegrass, creeping bentgrass, maize, and wheat, and dicots such as cotton, tomato, lettuce, *Arabidopsis*, tobacco, apple and geranium.

Plant transformation and cell culture: broadly refers to the process by which plant cells are genetically modified and transferred to an appropriate plant culture medium for maintenance, further growth, and/or further development. Such methods are well known to the skilled artisan.

Progeny: a "progeny" of the present invention, such as the progeny of a transgenic plant, is one that is born of, begotten by, or derived from a plant or the transgenic plant. Thus, a "progeny" plant, i.e., an "F1" generation plant is an offspring or a descendant of the transgenic plant produced by the inventive methods. A progeny of a transgenic plant may contain in at least one, some, or all of its cell genomes, the desired polynucleotide that was integrated into a cell of the parent transgenic plant by the methods described herein. Thus, the desired polynucleotide is "transmitted" or "inherited" by the progeny plant. The desired polynucleotide that is so inherited in the progeny plant may reside within a T-DNA construct, which also is inherited by the progeny plant from its parent. The term "progeny" as used herein also may be considered to be the offspring or descendants of a group of plants.

Promoter: is intended to mean a nucleic acid, preferably DNA, that binds RNA polymerase and/or other transcription regulatory elements. As with any promoter, the promoter sequences of the current present invention will facilitate or control the transcription of DNA or RNA to generate an mRNA molecule from a nucleic acid molecule that is operably linked to the promoter. As stated earlier, the RNA generated may code for a protein or polypeptide or may code for an RNA interfering, or antisense molecule.

A promoter, as used herein, may also include regulatory elements. Conversely, a regulatory element may also be separate from a promoter. Regulatory elements confer a number of important characteristics upon a promoter region. Some elements bind transcription factors that enhance the rate of transcription of the operably linked nucleic acid. Other elements bind repressors that inhibit transcription activity. The effect of transcription factors on promoter activity may determine whether the promoter activity is high or low, i.e. whether the promoter is "strong" or "weak."

A plant promoter is a promoter capable of initiating transcription in plant cells, whether or not its origin is a plant cell. Exemplary plant promoters include, but are not limited to, those that are obtained from plants, plant viruses, and bacteria such as *Agrobacterium* or *Rhizobium* which comprise genes expressed in plant cells. Examples of promoters under developmental control include promoters that preferentially initiate transcription in certain tissues, such as xylem, leaves, roots, or seeds. Such promoters are referred to as tissue preferred promoters. Promoters which initiate transcription only in certain tissues are referred to as tissue specific promoters. A cell type specific promoter primarily drives expression in certain cell types in one or more organs, for example, vascular cells in roots or leaves. An inducible or repressible promoter is a promoter which is under environmental control. Examples of environmental conditions that may effect transcription by inducible promoters include anaerobic conditions or the presence of light. Tissue specific, tissue preferred, cell type specific, and inducible promoters constitute the class of non-constitutive promoters. A constitutive promoter is a promoter which is active under most environmental conditions, and in most plant parts.

Polynucleotide is a nucleotide sequence comprising a gene coding sequence or a fragment thereof (comprising at least 15 consecutive nucleotides, at least 30 consecutive nucleotides, or at least 50 consecutive nucleotides), a promoter, an intron, an enhancer region, a polyadenylation site, a translation initiation site, 5' or 3' untranslated regions, a reporter gene, a selectable marker or the like. The polynucleotide may comprise single stranded or double stranded DNA or RNA. The polynucleotide may comprise modified bases or a modified backbone. The polynucleotide may be genomic, an RNA transcript (such as an mRNA) or a processed nucleotide sequence (such as a cDNA). The polynucleotide may comprise a sequence in either sense or antisense orientations.

An isolated polynucleotide is a polynucleotide sequence that is not in its native state, e.g., the polynucleotide is comprised of a nucleotide sequence not found in nature, or the polynucleotide is separated from nucleotide sequences to which it typically is in proximity, or is in proximity to nucleotide sequences with which it typically is not in proximity.

Regenerability: as used herein, refers to the ability of a plant to redifferentiate from a de-differentiated tissue.

Seed: a "seed" may be regarded as a ripened plant ovule containing an embryo, and a propagative part of a plant, as a tuber or spore. Seed may be incubated prior to *Agrobacterium*-mediated transformation, in the dark, for instance, to facilitate germination. Seed also may be sterilized prior to incubation, such as by brief treatment with bleach. The resultant seedling can then be exposed to a desired strain of *Agrobacterium*.

Selectable/screenable marker: a gene that, if expressed in plants or plant tissues, makes it possible to distinguish them from other plants or plant tissues that do not express that gene. Screening procedures may require assays for expression of proteins encoded by the screenable marker gene. Examples of such markers include the beta glucuronidase (GUS) gene and the luciferase (LUX) gene. Examples of selectable markers include the neomycin phosphotransferase (NPTII) gene encoding kanamycin and geneticin resistance, the hygromycin phosphotransferase (HPT or APHIV) gene encoding resistance to hygromycin, acetolactate synthase (a/s) genes encoding resistance to sulfonylurea-type herbicides, genes (BAR and/or PAT) coding for resistance to herbicides which act to inhibit the action of glutamine synthase such as phosphinothricin (Liberty or Basta), or other similar genes known in the art.

Sequence identity: as used herein, "sequence identity" or "identity" in the context of two nucleic acid or polypeptide sequences includes reference to the residues in the two sequences which are the same when aligned for maximum correspondence over a specified region.

As used herein, percentage of sequence identity means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

Transcription factor: Transcription factor refers to a polypeptide sequence that regulates the expression of a gene or genes by either directly binding to one or more nucleotide sequences associated with a gene coding sequence or indirectly affecting the activity of another polypeptide(s) that bind directly to one or more nucleotide sequences associated with a gene coding sequence. A transcription factor may activate (up-regulate) or repress (down-regulate) expression of a gene or genes. A transcription factor may contain a DNA binding domain, an activation domain, or a domain for protein-protein interactions. In the present invention, a transcription factor is capable of at least one of (1) binding to a nucleic acid sequence or (2) regulating expression of a gene in a plant. Additionally, the inventive polynucleotide sequences and the corresponding polypeptide sequences function as transcription factors in any plant species, including angiosperms and gymnosperms.

Transcription and translation terminators: The expression DNA constructs of the present invention typically have a transcriptional termination region at the opposite end from the transcription initiation regulatory element. The transcriptional termination region may be selected, for stability of the mRNA to enhance expression and/or for the addition of polyadenylation tails added to the gene transcription product.

Transfer DNA (T-DNA): an *Agrobacterium* T-DNA is a genetic element that is well-known as an element capable of integrating a nucleotide sequence contained within its borders into another genome. In this respect, a T-DNA is flanked, typically, by two "border" sequences. A desired polynucleotide of the present invention and a selectable marker may be positioned between the left border-like sequence and the right border-like sequence of a T-DNA. The desired polynucleotide and selectable marker contained within the T-DNA may be operably linked to a variety of different, plant-specific (i.e., native), or foreign nucleic acids, like promoter and terminator regulatory elements that facilitate its expression, i.e., transcription and/or translation of the DNA sequence encoded by the desired polynucleotide or selectable marker.

Transformation of plant cells: A process by which a nucleic acid is stably inserted into the genome of a plant cell. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, microinjection, polyethylene glycol-treatment, heat shock, lipofection and particle bombardment.

Transgenic plant: a transgenic plant of the present invention is one that comprises at least one cell genome in which an exogenous nucleic acid has been stably integrated. According to the present invention, a transgenic plant is a plant that may comprise only one genetically modified cell and cell genome, or it may comprise several or many genetically modified cells, or all of the cells may be genetically modified. A transgenic plant of the present invention may be one in which expression of the desired polynucleotide, i.e., the exogenous nucleic acid, occurs in only certain parts of the plant. Thus, a transgenic plant may contain only genetically modified cells in certain parts of its structure.

Variant: a "variant," as used herein, is understood to mean a nucleotide sequence that deviates from the reference (i.e., native, standard, or given) nucleotide sequence of a particular gene. The terms, "isoform," "isotype," and "analog" also refer to "variant" forms of a nucleotide sequence.

"Variant" may also refer to a "shuffled gene" such as those described in Maxygen-assigned patents. For instance, a variant of the present invention may include variants of sequences and desired polynucleotides that are modified according to the methods and rationale disclosed in U.S. Pat. No. 6,132,970, which is incorporated herein by reference.

Wood composition, as used herein, refers to a trait that can be modified to change the structure, appearance, or use of wood. While not limiting, traits that determine wood composition include cell wall thickness, cell length, cell size, lumen size, cell density, microfibril angle, tensile strength, tear strength, wood color, and length and frequency of cell division.

Wood pulp refers to fiber generated from wood having varying degrees of purification. Wood pulp can be used for producing paper, paper board, and chemical products.

It is understood that the present invention is not limited to the particular methodology, protocols, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a gene" is a reference to one or more genes and includes equivalents thereof known to those skilled in the art and so forth. Indeed, one skilled in the art can use the methods described herein to express any native gene (known presently or subsequently) in plant host systems.

Polynucleotide Sequences

The present invention relates to isolated nucleic molecules comprising a polynucleotide having a sequence selected from any of the polynucleotide sequences of SEQ ID NO: 1-7. The invention also provides functional fragments of the polynucleotide sequences of SEQ ID NO: 1-7. The invention further provides complementary nucleic acids, or fragments thereof, to any of the polynucleotide sequences of SEQ ID NO: 1-7, including nucleic acids complementary to the complete sequences of any of SEQ ID NO: 1-7, and nucleic acids that are the reverse complements of any of SEQ ID NO: 1-7, as well as nucleic acids comprising at least 15 contiguous bases which hybridize to any of the polynucleotide sequences of SEQ ID NO: 1-7.

By "isolated" nucleic acid molecule(s) is intended a nucleic acid molecule, DNA or RNA, which has been removed from its native environment. For example, recombinant DNA molecules contained in a DNA construct are considered isolated for the purposes of the present invention. Further examples of isolated DNA molecules include recombinant DNA molecules maintained in heterologous host cells or purified (partially or substantially) DNA molecules in solution. Isolated RNA molecules include in vitro RNA transcripts of the DNA molecules of the present invention. Isolated nucleic acid molecules according to the present invention further include such molecules produced synthetically.

Nucleic acid molecules of the present invention may be in the form of RNA, such as mRNA, or in the form of DNA, including, for instance, cDNA and genomic DNA obtained by cloning or produced synthetically. The DNA or RNA may be double-stranded or single-stranded. Single-stranded DNA may be the coding strand, also known as the sense strand, or it may be the non-coding strand, also referred to as the antisense strand.

Unless otherwise indicated, all nucleotide sequences determined by sequencing a DNA molecule herein were determined using an automated DNA sequencer (such as the Model 373 from Applied Biosystems, Inc.) by translation of a DNA. Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. Therefore, should any of SEQ ID NO: 1-7 contain a sequencing error, the present invention includes the actual nucleotide sequences of the sequenced DNA molecule, i.e., of the *Eucalyptus grandis* COMT promoter. As is also known in the art, a single insertion or deletion in a determined nucleotide sequence compared to the actual sequence will cause a frame shift in translation of the nucleotide sequence such that the predicted amino acid sequence encoded by a determined nucleotide sequence may be completely different from the amino acid sequence actually encoded by the sequenced DNA molecule, beginning at the point of such an insertion or deletion.

Each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U).

The present invention is also directed to fragments of the isolated nucleic acid molecules described herein. By a fragment of an isolated DNA molecule having the polynucleotide sequences shown in of SEQ ID NO: 1-7 is intended DNA fragments at least 15 nucleotides, at least 20 nucleotides, or at least 30 nucleotides in length, which are useful as diagnostic probes and primers as discussed in more detail below. Of course larger nucleic acid fragments of up to the entire length of the nucleic acid molecules of the present invention are also useful diagnostically as probes, according to conventional hybridization techniques, or as primers for amplification of a target sequence by the polymerase chain reaction (PCR), as described, for instance, in Molecular Cloning, A Laboratory Manual, 3rd. edition, edited by Sambrook & Russel., (2001), Cold Spring Harbor Laboratory Press, the entire disclosure of which is hereby incorporated herein by reference. By a fragment at least 20 nucleotides in length, for example, is intended fragments which include 20 or more contiguous bases from the nucleotide sequences of any one of SEQ ID NO: 1-7.

The nucleic acids comprising the nucleotide sequences of any one of SEQ ID NO: 1-7 can be generated using conventional methods of DNA synthesis which will be routine to the skilled artisan. For example, restriction endonuclease cleavage or shearing by sonication could easily be used to generate fragments of various sizes from larger sequences containing the sequences of interest, including the COMT promoter. Alternatively, the DNA sequences of the present invention could be generated synthetically according to known techniques.

In another aspect, the invention provides an isolated nucleic acid molecule comprising a polynucleotide which hybridizes under stringent hybridization conditions to at least a portion of a polynucleotide in a nucleic acid molecule of the invention described above. By a polynucleotide which hybridizes to a "portion" of a polynucleotide is intended a polynucleotide (either DNA or RNA) hybridizing to at least about 15 nucleotides, at least about 20 nucleotides, at least about 30 nucleotides, or more than 30 nucleotides of the reference polynucleotide. Nucleic acid molecules that hybridize to the reference polynucleotides are useful as diagnostic probes and primers.

A probe, as used herein is defined as at least about 20 contiguous bases of one of the nucleic acid sequences set forth in of SEQ ID NO: 1-7. For the purpose of the invention, two sequences hybridize when they form a double-stranded complex in a hybridization solution of 6×SSC, 0.5% SDS, 5×Denhardt's solution and 100 µg of non-specific carrier DNA. See Ausubel et al., section 2.9, supplement 27 (1994). Sequences may hybridize at "moderate stringency," which is defined as a temperature of 60° C. in a hybridization solution of 6×SSC, 0.5% SDS, 5×Denhardt's solution and 100 µg of non-specific carrier DNA. For "high stringency" hybridization, the temperature is increased to 68° C. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 h. For high stringency, the wash temperature is increased to 68° C. For the purpose of the invention, hybridized nucleotides are those that are detected using 1 ng of a radiolabeled probe having a specific radioactivity of 10,000 cpm/ng, where the hybridized nucleotides are clearly visible following exposure to X-ray film at −70° C. for no more than 72 hours.

The present application is directed to such nucleic acid molecules which are at least 60%, 65%, 70%, 75%, 80%, 85%, 90%, 95%, 96%, 97%, 98%, 99% or 100% identical to a nucleic acid sequence described in of SEQ ID NO: 1-7. One embodiment encompasses nucleic acid molecules which are at least 95%, 96%, 97%, 98%, 99% or 100% identical to the nucleic acid sequence shown in any of SEQ ID NO: 1-7. Differences between two nucleic acid sequences may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to a reference nucleotide sequence refers to a comparison made between two molecules using standard algorithms well known in the art and can be determined conventionally using publicly available computer programs such as the BLASTN algorithm. See Altschul et al., *Nucleic Acids Res.* 25:3389-3402 (1997).

Polynucleotides may be analyzed using the BLASTX algorithm, which compares the six-frame conceptual translation products of a nucleotide query sequence (both strands) against a protein sequence database. The similarity of polypeptide sequences may be examined using the BLASTP algorithm. The BLASTN, BLASTX and BLASTP programs are available on the NCBI anonymous FTP server under/blast/executables, and from the National Center for Biotechnology Information (NCBI) National Library of Medicine, Building 38A, Room 8N805, Bethesda, Md. 20894, USA. The BLASTN algorithm Version 2.0.4 [Feb.-24-1998] and Version 2.0.6 [Sep.-16-1998], set to the default parameters described in the documentation and distributed with the algorithm, are suitable for use in the determination of polynucleotide variants according to the present invention. The BLASTP algorithm is suitable for use in the determination of polypeptide variants according to the present invention. The BLAST family of algorithms, including BLASTN, BLASTP, and BLASTX, is described at NCBI's Internet website. The computer algorithm FASTA is available on the Internet at the University of Virginia FASTA server, and from the University of Virginia by contacting David Hudson, Assistance Provost for Research, University of Virginia, PO Box 9025, Charlottesville, Va. Version 2.0u4 [February 1996], set to the default parameters described in the documentation and distributed with the algorithm, may be used in the determination of variants according to the present invention. The use of the FASTA algorithm is described in Pearson and Lipman, *Proc. Natl. Acad. Sci. USA* 85:2444-2448, 1988; and Pearson, *Methods in Enzymol.* 183:63-98, 1990.

The following running parameters are suitable for determination of alignments and similarities using BLASTN that contribute to the E values and percentage identity for polynucleotide sequences: Unix running command: blastall -p blastn -d embldb -e 10 -G0 -E0 -r 1 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (blastn only) [Integer]; -v Number of one-line descriptions (V) [Integer]; -b Number of alignments to show (B) [Integer]; -i Query File [File In]; and -o LAST report Output File [File Out] Optional.

The following running parameters are suitable for determination of alignments and similarities using BLASTP that contribute to the E values and percentage identity of polypeptide sequences: blastall -p blastp -d swissprotdb -e 10 -G 0 -E 0 -v 30 -b 30 -i queryseq -o results; wherein the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA and BLASTP algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN, FASTA, or BLASTP algorithms set at parameters described above.

Alternatively, variant polynucleotides of the present invention hybridize to the polynucleotide sequences recited in of SEQ ID NO: 1-7, or complements, reverse sequences, or reverse complements of those sequences, under stringent conditions.

The present invention also encompasses polynucleotides that differ from the disclosed sequences but that, as a consequence of the degeneracy of the genetic code, encode a polypeptide which is the same as that encoded by a polynucleotide of the present invention. Thus, polynucleotides comprising sequences that differ from the polynucleotide sequences recited in of SEQ ID NO: 1-7; or complements, reverse sequences, or reverse complements thereof, as a result of conservative substitutions are contemplated by and encompassed within the present invention. Additionally, polynucleotides comprising sequences that differ from the polynucleotide sequences recited in of SEQ ID NO: 1-7, or complements, reverse complements or reverse sequences thereof, as a result of deletions and/or insertions totaling less than 10% of the total sequence length are also contemplated by and encompassed within the present invention.

Promoters

The polynucleotides of the present invention can be used for specifically directing the expression of polypeptides or proteins in the tissues of plants. The nucleic acids of the present invention can also be used for specifically directing the expression of antisense RNA, or RNA involved in RNA interference (RNAi) such as small interfering RNA (siRNA), in the tissues of plants, which can be useful for inhibiting or completely blocking the expression of targeted genes.

As used herein, vascular plant tissue refers to xylem, phloem or vascular cambium tissue. In one embodiment, the promoters of the invention may be "xylem-preferred," "cambium-preferred" or "phloem-preferred" and direct expression of an operably linked nucleic acid segment in the xylem, cambium or phloem, respectively. As used herein, "coding product" is intended to mean the ultimate product of the nucleic acid that is operably linked to the promoters. For example, a protein or polypeptide is a coding product, as well as antisense RNA or siRNA which is the ultimate product of the nucleic acid coding for the antisense RNA. The coding product may also be non-translated mRNA. The terms polypeptide and protein are used interchangeably herein. Xylem-preferred, for example, is intended to mean that the nucleic acid molecules of the current invention are more active in the xylem than in any other plant tissue. The nucleic acids of the current invention may be, for example promoters that are active specifically in the xylem, cambium or phloem, meaning that the promoters are only active in the xylem, cambium or phloem tissue of plants, respectively. In other words, a "xylem-specific" promoter, for example, drives the expression of a coding product such that detectable levels of the coding product are expressed only in xylem tissue of a plant. However, because of solute transport in plants, the coding product that is specifically expressed in the xylem, phloem or cambium may be found anywhere in the plant and thus its presence is not necessarily confined to xylem tissue. A vascular-preferred promoter, on the other hand can be preferentially active is any of the xylem, phloem or cambium tissues, or in at least two of the three tissue types. A vascular-specific promoter, is specifically active in any of the xylem, phloem or cambium, or in at least two of the three.

As used herein, "promoter" is intended to mean a nucleic acid, such as DNA, that binds RNA polymerase and/or other transcription regulatory elements. As with any promoter, the promoters of the current invention will facilitate or control the transcription of DNA or RNA to generate an mRNA molecule from a nucleic acid molecule that is operably linked to the promoter. The RNA may code for a protein or polypeptide or may code for an RNA interfering, or antisense molecule. As used herein, "operably linked" is meant to refer to the chemical fusion, ligation, or synthesis of DNA such that a promoter-nucleic acid sequence combination is formed in a proper orientation for the nucleic acid sequence to be transcribed into an RNA segment. The promoters of the current invention may also contain some or all of the 5' untranslated region (5' UTR) of the resulting mRNA transcript. On the other hand, the promoters of the current invention do not necessarily need to possess any of the 5' UTR.

In one embodiment, the promoters described herein are deletion fragments of the *Eucalyptus grandis* COMT promoter, such as any one of SEQ ID NO: 1-7. In accordance with that embodiment, the promoter sequences of the invention do not include the full-length COMT promoter sequences disclosed in WO 01/98485 and U.S. application Ser. No. 10/137,036.

DNA Constructs

The present invention provides DNA constructs comprising the isolated nucleic acid molecules of the present invention. In one embodiment, the DNA constructs of the present invention are Ti-plasmids derived from *A. tumefaciens*.

In developing the nucleic acid constructs of this invention, the various components of the construct or fragments thereof may be inserted into a convenient cloning vector, e.g., a plasmid that is capable of replication in a bacterial host, e.g., *E. coli*. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. to tailor the components of the desired sequence. Once the construct has been completed, it may then be transferred to an appropriate vector for further manipulation in accordance with the manner of transformation of the host cell.

A recombinant DNA molecule of the invention may include a selectable marker so that transformed cells can be easily identified and selected from non-transformed cells. Examples of such markers include, but are not limited to, a neomycin phosphotransferase (nptII) gene (Potrykus et al., *Mol. Gen. Genet.* 199:183-188 (1985)), which confers kanamycin resistance. Cells expressing the nptII gene can be selected using an appropriate antibiotic such as kanamycin or G418. Other commonly used selectable markers include the bar gene, which confers bialaphos resistance; a mutant EPSP synthase gene (Hinchee et al., *Bio/Technology* 6:915-922 (1988)), which confers glyphosate resistance; and a mutant acetolactate synthase gene (ALS), which confers imidazolinone or sulphonylurea resistance (European Patent Application 154,204, 1985).

Additionally, vectors may include an origin of replication (replicons) for a particular host cell. Various prokaryotic replicons are known to those skilled in the art, and function to direct autonomous replication and maintenance of a recombinant molecule in a prokaryotic host cell.

In one embodiment, the present invention utilizes a vector comprising the same backbone (pWVR8) as most of the constructs used in, for example, "Method for *Eucalyptus* Transformation," Attorney Docket Number 044463/0183, filed Jun. 6, 2003, which is incorporated by reference in its entirety.

In another embodiment, pART27 is suitable for use in the present invention. See Gleave, A. P. *Plant Mol. Biol,* 20:1203-1027 (1992).

The vectors may contain selectable markers for selection in plant cells. Numerous selectable markers for use in selecting transfected plant cells are known, including, but not limited to, kanamycin, glyphosate resistance genes, and tetracycline or ampicillin resistance for culturing in *E. coli, A. tumefaciens* and other bacteria.

For secretion of the translated protein into the lumen of the endoplasmic reticulum, the periplasmic space or into the extracellular environment, appropriate secretion signals may be incorporated into the expressed polypeptide. The signals may be endogenous to the polypeptide or they may be heterologous signals.

In one embodiment, a DNA construct of the current invention is designed in a manner such that an inventive polynucleotide sequence described herein is operably linked to a second polynucleotide sequence, wherein the inventive polynucleotide sequence regulates expression of the second polynucleotide sequence. In one embodiment, the second polynucleotide sequence encodes a polypeptide involved in cellulose or lignin biosynthesis in plants. Polynucleotides encoding many of the enzymes involved in lignin biosynthesis are known and include, but are not limited to, cinnamyl alcohol dehydrogenase (CAD), cinnamate 4-hydroxylase (C4H), coumarate 3-hydroxylase (C3H), phenolase (PNL), O-methyl transferase (OMT), cinnamoyl-CoA reductase (CCR), phenylalanine ammonia-lyase (PAL), 4-coumarate: CoA ligase (4CL) and peroxidase (POX) from pine. U.S. Pat. No. 6,204,434. Other enzymes include coniferin β-glucosidase (CBG), Sinapyl Alcohol Dehydrogenase (SAD), and caffeic acid 3-O-methyltransferase (COMT). U.S. Pat. No. 5,451,514, WO 94/23044, and Dharmawardhana et al., *Plant Mol. Biol.* 40: 365-72 (1999).

In another embodiment, the polynucleotide sequence of the present invention is operably linked to a coding sequence that inhibits the expression or activity of an enzyme involved in lignin biosynthesis. For example, of particular interest for control of lignin biosynthesis is an antisense gene encoding a 4CL, CAD, Lim, TED2, or a COMT.

In a further embodiment, the DNA constructs of the current invention are designed such that the polynucleotide sequences of the current invention are operably linked to DNA or RNA that encodes antisense RNA or interfering RNA, which corresponds to genes that code for polypeptides of interest, resulting in a decreased expression of targeted gene products. For example, the gene products targeted for suppression may be enzymes involved in lignin biosynthesis. The use of RNAi inhibition of gene expression is described in U.S. Pat. No. 6,506,559, and the use of RNAi to inhibit gene expression in plants is specifically described in WO 99/61631, both of which are herein incorporated by reference.

The use of antisense technology to reduce or inhibit the expression of specific plant genes has been described, for example in European Patent Publication No. 271988. Reduction of gene expression led to a change in the phenotype of the plant, either at the level of gross visible phenotypic difference, for example a lack of lycopene synthesis in the fruit of tomato leading to the production of yellow rather than red fruit, or at a more subtle biochemical level, for example, a change in the amount of polygalacturonase and reduction in depolymerisation of pectins during tomato fruit ripening (Smith et. al., *Nature*, 334:724-726 (1988); Smith et. al., *Plant Mol. Biol.*, 14:369-379 (1990)). Thus, antisense RNA has been demonstrated to be useful in achieving reduction of gene expression in plants.

In one embodiment, the inventive polynucleotide sequence is operably linked to a polynucleotide sequence that is capable of being transcribed inside a plant to yield an antisense RNA transcript. Transcription of the polynucleotide sequence in the plant cell generates an intracellular RNA transcript that is "antisense" with respect to that gene.

The invention also provides host cells which comprise the DNA constructs of the current invention. As used herein, a host cell refers to the cell in which the coding product is ultimately expressed. Accordingly, a host cell can be an individual cell, a cell culture or cells as part of an organism. The host cell can also be a portion of an embryo, endosperm, sperm or egg cell, or a fertilized egg.

Accordingly, the present invention also provides plants or plant cells, comprising the DNA constructs of the current invention. The invention includes plants such as angiosperms or gymnosperms. The expression construct of the present invention may be used to transform a variety of plants, both monocotyledonous (e.g. grasses, corn, grains, oat, wheat and barley), dicotyledonous (e.g., *Arabidopsis*, tobacco, legumes, alfalfa, oaks, eucalyptus, maple), and Gymnosperms (e.g., Scots pine; see Aronen, *Finnish Forest Res. Papers*, Vol. 595, 1996), white spruce (Ellis et al., *Biotechnology* 11:84-89, 1993), and larch (Huang et al., *In Vitro Cell* 27:201-207, 1991).

In one embodiment, the inventive expression vectors are employed to transform woody plants, herein defined as a tree or shrub whose stem lives for a number of years and increases in diameter each year by the addition of woody tissue. The target plant is optionally selected from the group consisting of eucalyptus and pine species, including *Eucalyptus grandis* and its hybrids, and *Pinus taeda*. Alternatively, the target plant is selected from the group consisting of *Pinus banksiana, Pinus brutia, Pinus caribaea, Pinus clasusa, Pinus contorta, Pinus coulteri, Pinus echinata, Pinus eldarica, Pinus ellioti, Pinus jeffreyi, Pinus lambertiana, Pinus massoniana, Pinus monticola, Pinus nigra, Pinus palustrus, pinus pinaster, Pinus ponderosa, Pinus radiata, Pinus resinosa, Pinus rigida, Pinus serotina, Pinus strobus, Pinus sylvestris, Pinus taeda, Pinus virginiana, Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Juniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata, Eucalyptus alba, Eucalyptus bancroftii, Eucalyptus botryoides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-angelica, Eucalyptus obliqua, Eucalyptus occidentalis Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo,* and *Eucalyptus youmanni.*

In particular, the transgenic plant may be of the species *Eucalyptus grandis* or its hybrids, *Pinus radiata, Pinus taeda* L (loblolly pine), *Populus nigra, Populus deltoides, Populus alba,* or *Populus* hybrids, *Acacia mangium,* or *Liquidamber styraciflua*. Wood and wood pulp obtained from such transformed plants also are included in the invention.

Beyond the ordinary meaning of plant, the term "plants" is also intended to mean the fruit, seeds, flower, strobilus etc. of the plant or somatic embryos, tissue cultures, cuttings, or other vegetative propagules derived from the plant. The plant of the current invention may be a direct transfectant, meaning that the DNA construct was introduced directly into the plant, such as through *Agrobacterium*, or the plant may the progeny of a transfected plant. The second or subsequent generation plant may or may not be produced by sexual reproduction, i.e., fertilization. Furthermore, the plant can be a gametophyte (haploid stage) or a sporophyte (diploid stage).

Functional Variants or Fragments of the Promoters of the Invention

Functional variants or fragments, as used herein, are nucleic acids that have a nucleic acid sequence at least about 70% identical to the reference nucleic acid, and that exhibit expression specificity substantially the same as that of the reference nucleic acid towards the same tissue as the reference nucleic acid. A functional variant need not exhibit the same degree of expression specificity as the reference nucleic acid, as long as it exhibits the same qualitative type of expression specificity, such as preference or specificity for the same tissue type or the same vascular preference. In one embodiment, the sequence of the functional variant or fragment is at least about 75% identical to the reference nucleic acid. In other embodiments, the sequence of the functional variant or fragment is at least about 80%, 85%, 86%, 87%, 88%, 89%, 90%, 91%, 92%, 93%, 94%, 95%, 96%, 97%, 98% or 99%.

As discussed in more detail in the examples below, the inventive polynucleotide sequences confer vascular-preferred gene expression. Functional variants of SEQ ID NO: 1-7, therefore, have a nucleic acid sequence at least about 70% identical to any of SEQ ID NO: 1-7 and also confer vascular-preferred gene expression.

Modifications that can produce functional variants may be made by sequential deletion of residues from the 5' end or the deletion of 5' UTR sequences from the 3' end. Alternatively, internal residues may be modified. Modifications that do not affect the function of the promoter regions most likely will be those that do not affect the binding of transcription factors.

The modifications encompassed by the invention also include those that occur naturally in the form of allelic variants of the promoters of the invention.

Methods of Making the Nucleic Acids of the Present Invention

The nucleic acids of the present invention can be obtained by using well-known synthetic techniques, standard recombinant methods, purification techniques, or combinations thereof. For example, the isolated polynucleotides of the present invention can be prepared by direct chemical synthesis using the solid phase phosphoramidite triester method (Beaucage et al., *Tetra. Letts.* 22:1859-1862 (1981)), an automated synthesizer (Van Devanter et al., *Nucleic Acids Res.* 12: 6159-6168 (1984)), or the solid support method of U.S. Pat. No. 4,458,066. Chemical synthesis generally produces a single stranded oligonucleotide, which can be converted into double stranded oligonucleotides by hybridization with a complementary sequence, or by polymerization, using the single strand as a template. Also, longer sequences may be obtained by the ligation of shorter sequences.

Alternatively, the nucleic acids of the present invention can be obtained by recombinant methods using mutually priming oligonucleotides. See e.g. Ausubel et al., (eds.), Current Protocols in Molecular Biology (John Wiley & Sons, Inc. 1990). Also, see Wosnick et al., Gene 60: 115 (1987); and Ausubel et al. (eds.), Short Protocols in Molecular Biology, 3$^{rd}$ ed., (John Wiley & Sons, Inc. 1995). Established techniques using the polymerase chain reaction provide the ability to synthesize polynucleotides at least 2 kilobases in length. Adang et al., Plant Mol. Biol. 21: 1131 (1993); Bambot et al., PCR Methods and Applications 2: 266 (1993); Dillon et al., "Use of the Polymerase Chain Reaction for the Rapid Construction of Synthetic Genes," in Methods In Molecular Biology, Vol. 15: PCR Protocols: Current Methods And Applications, White (ed.), pages 263-268, (Humana Press, Inc. 1993); Holowachuk et al., PCR Methods Appl. 4: 299 (1995).

Methods of Using the Nucleic Acids of the Invention

The nucleic acids of the current invention can be used for altering characteristics of a plant. The nucleic acids may be operably linked to a gene of interest to increase the levels of a molecule found in the vascular tissue. Alternatively, if the gene of interest inhibits the formation of an ultimate end product, the nucleic acids of the current invention can be used to decrease the levels of the product in vascular tissue.

One of the primary targets of such manipulated expression in the plant field is the lignin biosynthetic pathway. For the reasons set forth above, there is considerable interest in regulating the amount of lignin in plants, either positively or negatively, which can be accomplished through expression of gene products that impact this pathway. For example, manipulation of the number of copies of CAD and COMT modifies lignin content, as described in U.S. Pat. No. 5,451, 514 and WO 94/23044. Furthermore, antisense expression of sequences encoding CAD in poplar or pine leads to a modified lignin composition. Grand et al., *Planta* (Berl.) 163: 232-37 (1985); Baucher et al., Plant Physiol. 112: 1479 (1996), respectively. Thus, the present invention includes methods of altering the lignin content of plants using the promoter sequences of the invention, i.e., by transforming plant cells with DNA constructs comprising the sequences, and also includes plants and plant products, including wood and wood pulp, obtained by such methods.

The present invention, thus generally described, will be understood more readily by reference to the following examples, which are provided by way of illustration and are not intended to be limiting of the present invention.

EXAMPLES

Example 1

Isolation of a COMT Promoter from *Eucalyptus grandis*

Plant EST sequences homologous to a COMT gene were isolated and identified from *Eucalyptus grandis* cDNA expression libraries. *Eucalyptus grandis* cDNA expression libraries were prepared from mature shoot buds, early wood phloem, floral tissue, leaf tissue (two independent libraries), feeder roots, structural roots, xylem or early wood xylem and were constructed and screened as follows.

Total RNA was extracted from plant tissue using the protocol of Chang et al., *Plant Molecular Biology Reporter* 11:113-116 (1993) with minor modifications. Specifically, samples were dissolved in CPC-RNAXB (100 mM Tris-Cl, pH8.0; 25 mM EDTA; 2.0M NaCl; 2% CTAB; 2% PVP and 0.05% Spermidine*3HCl) and extracted with chloroform: isoamyl alcohol 24:1. RNA was precipitated with ethanol and purified using MessageMaker kit (Life Technologies). A cDNA expression library was constructed from purified mRNA by reverse transcriptase (Loopstra et al., *Plant Mol Biol.* 27:277-291 (1995)) synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µL of sample DNA from the 5 µL ligation mix. Mass excision of the library was done using XL 1-Blue MRF' cells and XLOLR cells (Stratagene) with ExAssist helper phage (Stratagene). The excised phagemids were diluted with NZY Broth (Gibco BRL, Gaithersburg, Md.) and plated out onto LB-kanamycin agar plates containing 5-bromo-4-chloro-3-indolyl-beta-D-galactoside (X-gal) and isopropylthio-beta-galactoside (IPTG).

Colonies were picked and DNA prepared using standard miniprep technology. Colonies containing a correct insert were cultured in NZY Broth with kanamycin and cDNA was purified by means of alkaline lysis and polyethylene glycol (PEG) precipitation. Agarose gel at 1% was used to screen sequencing templates for chromosomal contamination. Dye terminator chemistry was set up using Big Dye Chemistry (Applied Biosystems), according to the manufacturer's protocol.

The DNA sequence of positive clones were obtained using a 3700 Capillary Machine (Applied Biosystems) or a Prism 377 sequencer Perkin Elmer/Applied Biosystems Division. cDNA clones were sequenced first from the 5' end, and in some cases, also from the 3' end. For some clones internal sequence was obtained using subcloned fragments. Subcloning was performed using standard procedures of restriction mapping and subcloning into pBluescript II SK+ vector.

Polynucleotide sequences can be aligned with other polynucleotide and/or polypeptide sequences and the degree of shared identical sequence can be determined using computer algorithms that are publicly available. The BLAST family of algorithms, including BLASTN, BLASTP, and BLASTX, is described in the publication of Altschul et al., "Gapped BLAST and PSI-BLAST: a new generation of protein database search programs," *Nucleic Acids Res.* 25:3389-3402, 1997. The BLASTN algorithm Version 2.0.11 [Jan. 20, 2000] set to the default parameters described in the documentation and distributed with the algorithm, are suitable for use in the determination of polynucleotide variants according to the present invention.

BLASTX searches were performed using SWISSPROT-TREMBL Sequences [Jul. 9, 2002] and the searches were performed on Nov. 15, 2002. The following running parameters are suitable for the determination of alignments and similarities using BLASTX that contribute to the E values and percentage identity of polypeptide sequences: blastall -p blastx -d swissprotdb -e 10 -G 0 -E 0 -FF -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -F Filter Query Sequence [String]; -v Number of one-line descriptions (v) [Integer]; -b Number of alignments to show (b) [Integer]; -I Query File [File In]; -o BLAST report Output File [File Out] Optional.

Using the "Genome Walker" kit (Clontech, Palo Alto, Calif.) and gene-specific primers designed from the plant polynucleotide sequence, 5'UTR sequences containing the putative promoter of the *E. grandis* COMT gene were isolated from genomic DNA and were extended by further sequencing. The nucleotide sequence of the isolated COMT polynucleotide comprising the promoter region and coding region was identified and disclosed in U.S. Provisional Application No. 60/425,087, herein incorporated by reference.

Example 2

Functional Analysis of *Eucalyptus grandis* Caffeic acid 3-O-Methyl Transferase Promoter The xylem specific *Eucalyptus grandis* Caffeic acid 3-O-methyl transferase (COMT) promoter has been dissected into seven fragments (534, 485, 306, 293, 119, 99, and 66 bp) based on the location of putative cis-elements that appear in the isolated 1.7 kb promoter 5' fragment. These were designed based on the position of putative vascular specific and PAL/AC rich cis-elements in the promoter (GXXXXGTTG; *Plant Molecular Biology* 37: 977-988 1998 and CCATAAACCCC; *Plant Journal* 22: 289-301 2000). The nucleotide sequence of each promoter deletion is disclosed in below in FIGS. 1-7 (SEQ ID NO: 1-7).

Table 1 displays each promoter sequence and its homology, as determined by EMBL (EST and genomic) database on May 27, 2003.

Title 1

| SEQ ID NO: | Sequence Length (bp) | EMBL Homology | E value |
| --- | --- | --- | --- |
| 1 | 534 | *E. gunnii* OMT | 5e–05 |
| 2 | 485 | *E. gunnii* OMT | 4e–05 |
| 3 | 306 | *E. gunnii* OMT | 3e–05 |
| 4 | 293 | *E. gunnii* OMT | 2e–05 |
| 5 | 119 | *E. gunnii* OMT | 9e–06 |
| 6 | 99 | *E. gunnii* OMT | 7e–06 |
| 7 | 66 | *E. gunnii* OMT | 4e–06 |

Example 3

Methodology to Determine the Tissue Specificity of a Promoter

Following the identification and cloning of a promoter by the procedure outlined above, the promoter, or fragment thereof, is operably linked with a reporter gene to determine those tissue types in which the promoter is active. To this end, a construct containing the promoter first is transformed into *Agrobacterium tumefaciens* by electroporation. Briefly, 40 μl of diluted AgL-1 competent cells are placed on ice and are contacted with about 10 ng of pART27 vector containing the promoter sequence. Electroporation is conducted at the following parameters:

Resistance=129 ohm
Charging voltage=1.44 kV
Field strength=14.4 kV/cm
Pulse duration=5.0 ms Following electroporation, 400 μl of YEP liquid media is added and the cells are allowed to recover for one hour at room temperature. Cells then are centrifuged at 6000 rpm for 3 min and are resuspended in ~50 μl YEP. Cell samples are spread over the surface of a YEP Kan50/Rif50 plate, sealed with parafilm, and incubated at 29° C. for 2 days for colony growth.

Wild type *Arabidopsis thaliana* cv. 'Columbia-0' plants are then transformed with *Agrobacterium* containing constructs of interest by floral dip infiltration. Briefly, *Agrobacterium* cultures are centrifuged at ~8600 rcf for 10 min at 20° C. and are resuspended to an optical density of ~0.7-0.8. Plants are dipped into an infiltration solution containing the *Agrobacterium* for 5 sec. Plants are drained of excess solution and placed under grow lights in ambient conditions. After 24 hrs, the plants are misted and maintained for seed production. $T_1$ seeds are surface sterilized in 5% commercial bleach solution and plated on MS media containing Kanamycin (50 mg/l) and Timentin (250 mg/l) to select for putative transformants.

Successfully transformed plants are then assayed for the expression of the operably linked reporter gene. Leaf, stem, root and floral regions are immersed in a staining solution (50 mM NaPO$_4$, pH 7.2, 0.5% Triton X-100, 1 mM X-Glucuronide, cycloheximide salt (Ducheffa). A vacuum is applied twice for 5 min to infiltrate the tissue with the staining solution. The tissue is then left shaking overnight at 37° C. for color development. Tissues are checked at three or four timepoints to check stain development, and if samples show early development, a piece of tissue is destained in 70% ethanol. This tissue is then examined for GUS expression using a light microscope and photographed.

Example 4

In Planta Expression Data

As described in Example 3, transformed *Arabidopsis* and *N. benthamiana* tissues are analyzed for GUS reporter gene expression. To assay GUS expression, leaf, root, and floral materials are immersed in the GUS solution as described in Example 2. A vacuum is applied twice for 5 minutes to infiltrate the tissue with the staining solution and the tissue is then incubated overnight in a shaker at 37° C. for color development. Following overnight incubation, the tissue samples are then destained in 70% ethanol and examined under a light microscope for GUS expression. FIG. 2 displays the percentage of transformed *Arabidopsis* and *N. benthamiana* plants expressing GUS.

Three months post soil transfer, tissues from *N. benthamiana* $T_1$ plants are embedded into paraplast, sectioned with a microtome, and analyzed with a light microscope for GUS expression. The GUS localization and microtome results, as shown in Table 2, demonstrate that the disclosed isolated nucleotide sequences confer reporter gene expression preferentially in vascular cambium, xylem, and/or phloem tissues of transformed *Arabidopsis* and *N. benthamiana* plants.

TABLE 2

In planta GUS vascular expression

| SEQ ID NO | Size (bp) | No Plants GUS+ | No Plants Tested | % GUS Expression | GUS Vascular Localization | Microtome Results |
|---|---|---|---|---|---|---|
| 1 | 534 | 5 | 12 | 41.67 | Stem material | Xylem, differentiating Cambial cells |
| 2 | 485 | 10 | 12 | 83.33 | Stem, leaf veins | Cambial cells, primary xylem, xylem rays, pith |
| 3 | 306 | 9 | 12 | 75.00 | Stem | Primary and Secondary Xylem, differentiating Cambial cells, Phloem Fiber cells |
| 4 | 293 | 9 | 10 | 90.00 | Stem, developing lateral roots | Xylem, differentiating cambial cells, base and mid sections of xylem rays |
| 5 | 119 | 4 | 12 | 33.33 | Stem, branch points | Xylem |
| 6 | 99 | Not Tested | Not Tested | Not Tested | Not Tested | Not Tested |
| 7 | 66 | Not Tested | Not Tested | Not Tested | Not Tested | Not Tested |

*N. benthamiana* tissue samples are placed in a vial containing fixative solution (100% Ethanol, Glacial acetic acid, 37% Formaldehyde, mQH$_2$0) and a vacuum is applied twice for 15 minutes. The samples are incubated in the fixative solution for two hours to ensure tissue infiltration. Following tissue infiltration, a vacuum is reapplied for 15 minutes and the tissues are placed at 4° C. overnight.

Following overnight incubation, the tissue samples are dehydrated through a series of ethanol incubations, wherein all incubations occur at room temperature. The overnight fixative solution is removed from the vial containing the tissue samples and replaced with 50% ethanol. After 30 minutes, the 50% ethanol is decanted and the tissues are incubated in a fresh aliquot of 50% ethanol. After 30 minutes in 50% ethanol, the solution is removed and replaced with 60% ethanol. Following 30 minute incubation, 60% ethanol is replaced with 70% ethanol. The 70% ethanol is decanted after 30 minutes and replenished with 85% ethanol. Following 30 minute incubation, the 85% ethanol is removed and the samples are incubated overnight in 95% ethanol.

Following tissue dehydration, the tissues are incubated at room temperature in a series of xylene solutions. The overnight 95% ethanol solution is removed, and the tissues are incubated in 100% ethanol for 30 minutes. After 30 minutes, 100% ethanol is removed and the tissues are suspended in 25% Xylene:75% Ethanol. Following 30 minute incubation, the solution is replaced with 50% Xylene:50% Ethanol. The solution is then decanted and replenished with 75% Xylene:25% Ethanol. After 30 minutes, the tissues are thrice incubated in 100% Xylene for 60 minutes. The tissues are then overnight incubated in a vial containing xylene and 20 paraplast chips.

To infuse the paraffin, the vials are placed in a 42° C. hybridization oven until the paraplast chips dissolve. Throughout the course of 8 hours, a total of 60-80 paraffin chips are added to the vial and allowed to dissolve. The samples are left overnight in a 62° C. hybridization oven. Over the course of the next two days, the paraplast is changed four times, at 12 hour intervals. To embed the tissues, the liquid paraffin is poured into the cassette and the tissues are placed in the proper orientation. The cassette is then placed at 4° C. overnight to allow the paraffin to harden.

Example 5

Isolation and Culture of *Zinnia elegans* Mesophyll Cells in Tracheary Element (TE) Inducing (FKH) and Non-Inducing (FK) Medium Primary and secondary pair leaves from the *Zinnia* seedlings were harvested from 8 punnets. Leaves were sterilized in 500 ml of 0.175% sodium hypochlorite solution for 10 minutes. Leaves were then rinsed twice in 500 ml of sterile water. Using 20-30 leaves at a time, leaves were ground in mortar and pestle and 25-30 ml of FK medium. Cells were filtered through the 40 µm nylon mesh. A total of 90 ml of mesophyll cells were obtained in this fashion. Cells were pelleted by centrifuging at 200×g for 2 minutes at 20° C. The pellet was washed once more using equal volume of FK medium. Then the pellet was split in to two equal halves and one half was washed in 45 ml of FK medium and the other in 45 ml of FKH medium. The pellets were re-suspended in 60 ml of FK medium and 60 ml of FKH medium, respectively. They were cultured in the dark in two 6-well plates on the rotary shaker set at 120 rpm.

Example 6

Isolation of *Zinnia elegans* Protoplasts from Leaves or Mesophyll Cells Cultured Overnight to Three Days in FK Medium and FKH Medium Sterile *Zinnia elegans* primary leaves (6-8 in number) were cut in slivers of 1 mm and placed in 15 ml of cell wall digesting enzyme mix (1% Cellulase Onozuka R-10 and 0.2% pectolyase Y23 in Protoplast isolation buffer). Mesophyll cells cultured in FK medium (40 ml) or FKH medium (40 ml) were pelleted by centrifuging at 200×g for 2 minutes at 20° C. Each pellet was re-suspended in 20 ml of sterile Protoplast isolation buffer containing 200 mg Cellulase Onozuka R-10 and 40 mg Pectolyase Y23. The protoplasts were isolated by incubating the cell suspensions in CellStar culture plates for 2-4 hours on a rotary shaker set at ~70 rpm at 23° C. Protoplasts were pelleted by centrifuging the contents of the plates at 200×g for 2 minutes. Each of the pellets was re-suspended in 20 ml of 24% sucrose solution.

Example 7

Transfection of *Zinnia elegans* Protoplasts

*Zinnia* protoplasts in 24% sucrose solution were overlaid with 1 ml of W5 solution and centrifuged at 70×g for 10 minutes at 20° C. with brakes off. Floating protoplasts were harvested and resuspended in 10 ml of W5 solution. Protoplasts were pelleted by centrifuging at 70×g for 10 minutes at 20° C. Protoplasts were resuspended in MaMg medium (density=~5×10$^6$ protoplasts/ml) and aliquoted into individual 15 ml tubes (300 µl: 1.5×10$^6$ protoplasts). 5 µg DNA (of each construct) and 50 µg Salmon Testes DNA was added to the protoplast suspension, mixed and incubated for 5 minutes at 20° C. 300 µl 40% PEG solution was added to each aliquot of protoplasts, mixed and incubated for 20 minutes at 20° C. 5 ml of K3/0.4M sucrose was added to each aliquot of leaf-derived transfected protoplasts or transfected protoplasts from mesophyll cells cultured in FK medium and mixed. Similarly, 5 ml of K3/0.4M sucrose+0.1 ppm NAA+0.2 ppm BA was added to each aliquot of transfected protoplasts from mesophyll cells cultured in FKH medium and mixed. The transfected protoplast suspensions were incubated overnight at 23° C. in the dark.

Example 8

Harvesting of Transfected *Zinnia elegans* Protoplasts and Reporter Gene Analysis Transfected *Zinnia* protoplast suspensions prepared as described above in Examples 5-7 were individually harvested by adding 9.5 ml of W5 solution, mixing the contents of each tube and centrifuging at 70×g for 10 minutes at 20° C. The bulk of the supernatant was removed by decanting and the protoplasts volume was brought up to 900 µl. From this, 300 µL of protoplasts were aliquoted into 5 ml polystyrene round-bottom tubes, re-suspended in a volume of 500 µl W5 medium and set aside for analysis of fluorescent reporter gene expression and cell viability. The protoplasts and the remaining solution were transferred to individual microtubes and pelleted by centrifugation at 420×g for 2 minutes at 20° C. The protoplast pellet was assayed for GUS reporter gene expression as described by Jefferson, R. A., 1987, *Plant Mol. Biol. Rep.* 5, 387. GUS (MUG) assays were performed using a Wallac (Turku, Finland) Victor 21420 Multilabel Counter. Umbelliferone was detected using a 355 nm excitation filter and a 460 nm emission filter for 1 second.

Example 9

COMT Promoter Analysis Using TE Assay

As described in Examples 5-8, *Zinnia elegans* mesophyll cells were cultured in maintenance medium (FK) or TE inducing medium (FKH). Protoplasts were isolated and transformed with a plasmid containing the GUS (β-D-glucuronidase) reporter gene in frame with the specified *E. grandis* COMT promoter fragments. The constructs were tested, and the results are described below in Table 3.

TABLE 3

| SEQ ID NO: | Sequence Length (bp) | Relative level of activity in TE assay | Enhanced in TE-forming cells? |
|---|---|---|---|
| 1 | 534 | high | yes |
| 2 | 485 | high | yes |
| 3 | 306 | high | yes |
| 4 | 293 | high | yes |
| 5 | 119 | low | yes |
| 6 | 99 | low | yes |
| 7 | 66 | not detectable | no |

Example 10

COMT Promoter Deletion Analysis Reveals Presence of an Enhancer

As illustrated in Example 2, the isolated nucleotide sequences of the present invention confer GUS reporter gene expression preferentially in vascular cambium, xylem, and/or phloem tissues. However, as evidenced in Example 9 (FIG. 3), a pronounced reduction in promoter activity occurs when the proximal promoter is shortened from 306 bp to 119 bp. This data suggests that an enhancer element or elements are present in this region, and further, that the element is localized in the sequence between the 293 bp fragment and the 119 bp fragment.

As described in Examples 5-8, *Zinnia elegans* mesophyll cells were cultured in either TE-inducing or maintenance medium. Protoplasts were isolated and transformed with a plasmid containing the GUS (β-D-glucuronidase) reporter gene in frame with the specified *E. grandis* COMT promoter fragments. The constructs were assayed for GUS expression. As shown in FIG. 8, GUS expression is significantly reduced when the COMT promoter is truncated from 293 bp to 119 bp, indicating the presence of an enhancer element.

Example 11

Analysis of LIM Binding Site/PAL Box/AC Rich Box in the COMT Promoter

A consensus LIM binding site/PAL box/AC rich box was identified between base pairs 306 and 293 of the COMT promoter. The *Zinnia* TE assay, as described in Examples 5-8, was used to test (i) the effect of deleting a consensus LIM binding site/PAL box/AC rich box located between 306 and 293 bp and (ii) co-transfecting a plasmid that encodes a *Eucalyptus* LIM transcription factor.

Figure 9:
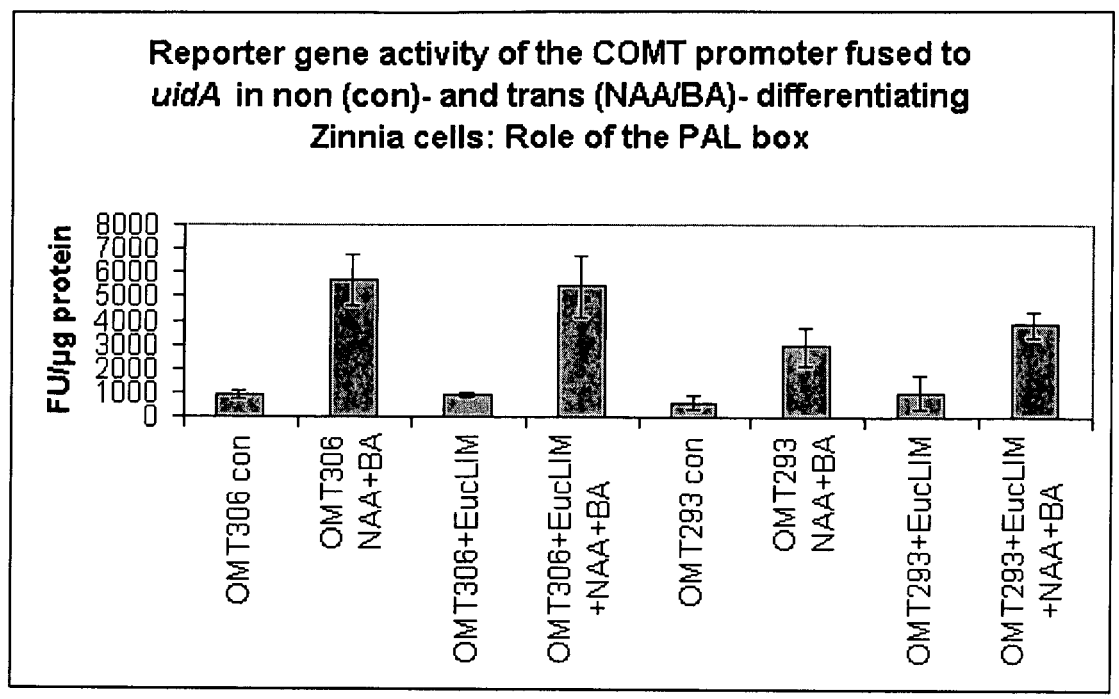
FIG. 9 displays deletion analysis of COMT promoter consensus LIM binding site/PAL box/AC rich box.

As illustrated in FIG. 9, deletion of the consensus LIM binding site/PAL box/AC rich box resulted in a minor reduction in reporter gene activity; however the presence of a *Eucalyptus* LIM transcription factor had little effect on reporter gene expression.

Example 12

Analysis of Minimal Vascular-Specific Region of COMT Promoter

Figure 10:
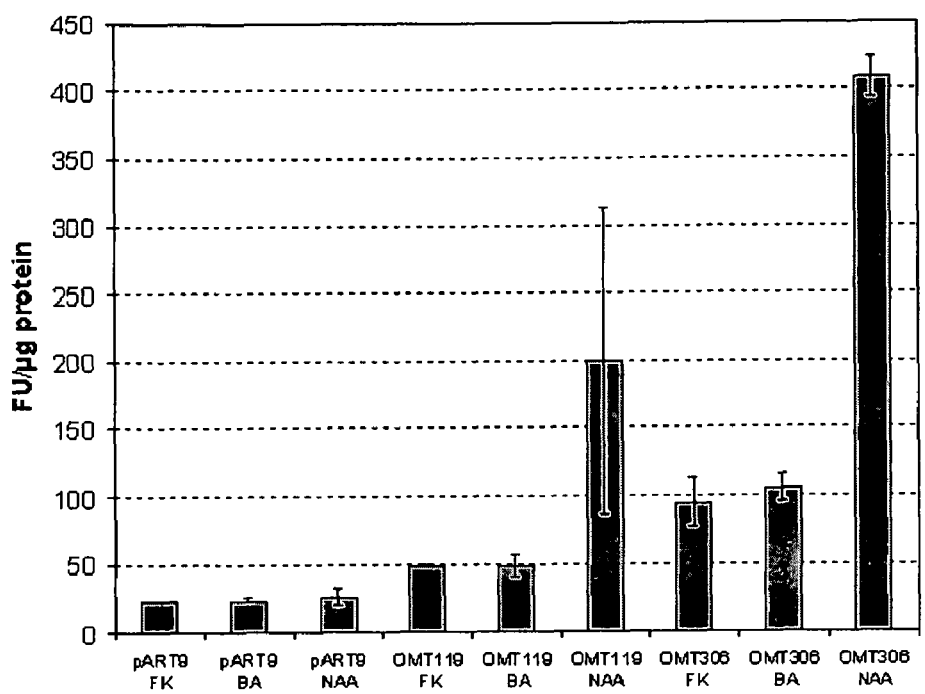
FIG. 10 displays COMT activity in response to plant growth regulators.

To understand the nature of the signal transduction pathway(s) regulating COMT expression, the minimal vascular-specific region of the COMT promoter was analyzed for responsiveness to auxin and cytokinin, independently. *Zinnia* mesophyll cells were transformed with a construct harboring either 306 bp or 119 bp promoter fragments operably linked to the GUS reporter gene. The cells were cultured in the presence of either auxin (NAA) or cytokinin (BA), and reporter gene expression was compared with cells cultured on hormone-free maintenance media (FK). As shown in FIG. 10, auxin is sufficient to induce promoter activity.

Example 13

Cell Based Assay Screening of Transcription Factors

Cell-based assays can be used for screening the function of promoters and transcription factors from the Pine and *Eucalyptus* databases. The assays are used to identify transcription factors that are active during tracheary differentiation and lignification by determining whether a promoter responds to trans-acting factors in plant cells that are either induced in tracheary element (TE) forming cells (endogenous factors) and/or introduced by transformation (transient assay after introduction of plasmid DNA into the cells). The assay comprises the isolation of *Zinnia elegans* mesophyll cells and their culture either in TE-inducing or maintenance medium. See Examples 5-8. Control promoterless constructs or constructs comprising promoters that are active during TE formation (linked to reporter genes) are introduced into the cells or protoplasts prepared from the cells. As described above in Example 8, the transfected protoplasts are harvested by centrifugation and assayed for viability and transgene expression. To correct for experimental variation that may arise from differences in transfection, the protoplasts are co-transfected with a transfection marker, which is also detected by flow cytometry. This system uses fluorescence analysis technologies to capture the data and informatics software to analyze the results. In this way the impact of an introduced gene or gene product can be monitored. Transcriptional repression or activation of a vascular-preferred Pine or *Eucalyptus* promoter, such as the COMT promoter and fragments thereof, can be attributed to the candidate transcription factor gene and may be used to support sequence data.

Example 14

Strong Transcriptional Activators of COMT Promoter

As described in Examples 1, *E. grandis* and *P. radiata* cDNA libraries were screened for nucleotide sequences of interest. Several transcription factor families were identified in these libraries and full-length sequences were cloned. Each transcription factor is then cloned in a DNA construct having a promoter operably linked to a reporter gene, wherein the transcription factor regulates the activity of the promoter-reporter gene fusion. Based on the expression level of a reporter gene, a transcription factor can be identified as a transcriptional activator or repressor, relative to a wild-type construct that does not contain a transcription factor sequence. Moreover, the transcription factor may be identified as strong or weak activator or repressor. A strong transcriptional activator causes an increase in reporter gene expression, relative to a wild-type construct. A weak transcriptional activator causes an increase in reporter gene expression, relative to a wild-type construct. Similarly, a strong transcriptional repressor causes a decrease in reporter gene expression, relative to a wild-type construct. A weak transcriptional repressor causes a decrease in reporter gene expression, relative to a wild-type construct. Table 4 below displays transcription factors having strong transcriptional activity with a specific promoter. Transcriptional Activity is quantified as a value between one and four, wherein a value of four represents an upward maximum of transcriptional activity.

TABLE 4

| Construct | Species | Transcription Factor Family | Promoter | Activator or Repressor | Transcriptional Activity |
|---|---|---|---|---|---|
| pFOR534 | P. radiata | AP2/EREBP | 306 bp COMT | Activator | 4 |
| pFOR538 | P. radiata | AP2/EREBP | 306 bp COMT | Activator | 2 |
| pFOR540 | P. radiata | AP2/EREBP | 306 bp COMT | Activator | 2 |
| pFOR542 | P. radiata | AP2/EREBP | 306 bp COMT | Activator | 2 |
| pFOR548 | P. radiata | AP2/EREBP | 306 bp COMT | Activator | 2 |
| pFOR549 | P. radiata | AP2/EREBP | 306 bp COMT | Activator | 2 |
| pFOR553 | P. radiata | AP2/EREBP | 306 bp COMT | Activator | 4 |
| pFOR502 | P. radiata | C2C2 DOF | 306 bp COMT | Activator | 2 |
| pFOR405 | P. radiata | MYB | 306 bp COMT | Activator | 3 |
| pFOR414 | P. radiata | MYB | 306 bp COMT | Activator | 2 |
| pFOR420 | P. radiata | MYB | 306 bp COMT | Activator | 2 |
| pFOR424 | P. radiata | MYB | 306 bp COMT | Activator | 2 |
| pFOR793 | P. radiata | SBP | 306 bp COMT | Activator | 3 |
| pFOR793 | P. radiata | TCP | 306 bp COMT | Activator | 4 |
| pFOR929 | P. radiata | TCP | 306 bp COMT | Activator | 3 |
| pFOR620 | E. grandis | AP2/EREBP | 306 bp COMT | Activator | 2 |
| pFOR476 | E. grandis | AP2/EREBP | 306 bp COMT | Activator | 2 |
| pFOR480 | E. grandis | AP2/EREBP | 306 bp COMT | Activator | 2 |
| pFOR481 | E. grandis | AP2/EREBP | 306 bp COMT | Activator | 2 |
| pFOR483 | E. grandis | AP2/EREBP | 306 bp COMT | Activator | 2 |
| pFOR614 | E. grandis | AP2/EREBP | 306 bp COMT | Activator | 2 |
| pFOR615 | E. grandis | AP2/EREBP | 306 bp COMT | Activator | 3 |
| pFOR618 | E. grandis | AP2/EREBP | 306 bp COMT | Activator | 2 |
| pFOR499 | E. grandis | bHLH | 306 bp COMT | Activator | 2 |
| pFOR641 | E. grandis | bHLH | 306 bp COMT | Activator | 3 |
| pFOR799 | E. grandis | GARP | 306 bp COMT | Activator | 2 |
| pFOR372 | E. grandis | MYB | 306 bp COMT | Activator | 5 |
| pFOR374 | E. grandis | MYB | 306 bp COMT | Activator | 4 |
| pFOR375 | E. grandis | MYB | 306 bp COMT | Activator | 2 |
| pFOR376 | E. grandis | MYB | 306 bp COMT | Activator | 3 |
| pFOR395 | E. grandis | MYB | 306 bp COMT | Activator | 4 |
| pFOR799 | E. grandis | GARP | 306 bp COMT | Activator | 2 |
| pFOR977 | E. grandis | TCP | 306 bp COMT | Activator | 3 |

Example 15

Transformation of *Eucalyptus camaldulensis* Clone C9 with COMT Promoter Sequences

*Eucalyptus camaldulensis* clone C9 was transformed with the inventive COMT promoter sequences. C9 stock materials were maintained as shoot clumps in Magenta boxes and subcultured every 4-6 weeks. Unless noted otherwise, all cultures were grown under shaded, cool fluorescent light with a light intensity of 30-40 µE/m$^2$/s with a photoperiod of 16 hours, and the temperature of the growth room was kept at 21° C.

The following constructs were used for the transformation experiments:

pWVK211—Euc OMT promoter fragment 485 bp:GUS (intron), UBQ10:NPTII (promoter-GUS construct is equivalent to pARB536)

pWVK212—Euc OMT promoter fragment 306 bp:GUS (intron), UBQ10:NPTII (promoter-GUS construct is equivalent to pARB537)

The GUS gene used in constructs pWVK211 and pWVK212 contain an intron so that GUS expression only occurs in plant cells and not in bacterial cells. The *Agrobacterium* strain GV2260 was used for the transformation studies.

Using methods known in the art. *Agrobacterium* GV2260 cells were transformed with pWVK211 and pWVK212 and the cells were grown on YEP medium (10 g/l yeast extract, 10 g/l peptone and 50 mg/l NaCl, pH 7.0-7.2) for 3 days. After 3 days, a single colony was selected and grown in 20-50 ml liquid YEP medium with kanamycin (100 mg/l) and rifampicin (50 mg/l). Cultures were incubated overnight in a shaking incubator at 28° C. and 150 rpm. The overnight culture with an OD of about 0.6-1.1 was spun down in a desktop centrifuge at 3000 g for 20 minutes and resuspended with *Agrobacterium* Induction Medium or AIM (WPM salts with glucose at 5 g/l, 250 µM acetosyringone, 2 mM phosphate buffer, and 0.05 M MES, pH 5.8) with OD of about 0.6-1.1. Cultures were incubated for 25 minutes at 28° C. before plant inoculation. Bacterial concentration was determined before and after inoculation.

Healthy and newly opened leaves of *Eucalyptus camaldulensis* clone C9 were selected for transformation. The tip portions of the leaves were removed by scissors or forceps to increase the number of wounded cells. Explants were prepared and placed on pre-culture/co-cultivation medium (as described in U.S. Provisional Application No. 60/476,222, filed Jun. 6, 2003), abaxial side down, the day before transformation.

Induced *Agrobacterium* culture was prepared as described above and was dripped onto each explant by pipettes. Sufficient *Agrobacterium* culture was dripped to ensure that all the cut edges were covered with bacterial solution. Explants covered with *Agrobacterium* culture were placed in dark for three days of co-cultivation. After the co-cultivation, the explants were directly transferred to selection medium (Euc Regeneration medium as described in U.S. Provisional Application No. 60/476,222). Explants are transferred to fresh selection medium every two weeks until shoots proliferated and initially elongated.

A PCR-based method was used to screen the selected antibiotic-resistant shoot lines. Specifically, PCR was employed to detect the antibiotic-resistant gene NPTII. Genomic DNA was isolated according to the protocol described by the Extract-N-Amp™ Plant PCR kit (Sigma) with the modification that three small leaves from each shoot line were isolated for DNA extraction. 4 µl total DNA was added to a 16 µl PCR reaction mixture containing 10 µl REDExtract-N-Amp reaction mix, 1 µl 20 µM NPTII forward primer, 1 µl 20 µM NPTII reverse primer, and 4 µl water. The PCR was performed as follows:

| Cycle 1: | 95° C. for 5 minutes |
| --- | --- |
|  | 60° C. for 1 minute |
|  | 72° C. for 1 minute |
| Cycles 2-30 | 95° C. for 1 minute |
|  | 60° C. for 1 minute |
|  | 72° C. for 1 minute |
| Cycle 31 | 95° C. for 1 minute |
|  | 60° C. for 1 minute |
|  | 72° C. for 10 minutes |

Following completion of PCR, the PCR amplification products were visualized on an agarose gel stained with ethidium bromide.

NPTII positive lines were identified and further screened for the presence of GUS gene with PCR. The protocol is the same as above except that the primers were specific for GUS gene and the PCR annealing temperature was 58° C., and the PCR products were amplified for 35 cycles.

GUS expression was also assayed when explants produced antibiotic-resistant calli and elongated shoots. To assay GUS expression, the explants were incubated in a substrate comprising 100 mM phosphate buffer (pH 7.0), 0.05% dimethyl sulphoxide, 0.05% Triton X-100, 10 mM EDTA, 0.5 mM potassium ferrocyanide, and 1.5 mg/ml 5-bromo-4-chloro-3-indolyl-β-D-glucuronide (X-gluc). The explants were subjected to 10 minutes of vacuum before an overnight incubation at 37° C. Following overnight incubation and destaining with methanol and ethanol, GUS positive samples were evaluated under a microscope accompanied with an image analysis system.

As shown below in Table 5, transformed callus tissue non-selectively expressed GUS. However, following shoot regeneration, plants transformed with the 485 bp promoter fragment displayed vascular-specific expression. Specifically, plants transformed with the 485 bp promoter fragment displayed strong GUS expression in the vascular tissue of the main stem of each shoot. Vascular-specific GUS expression was not detected in the plants transformed with the 306 bp promoter fragment.

TABLE 5

NPTII PCR Screening Results and GUS Staining Results.

| Construct | No. Lines Positive/No. Lines Assessed | | Percent GUS Positive Calli Lines/Calli Lines Assessed | No. Shoot Lines with Strong GUS Staining/No. Shoot Lines Assessed |
| --- | --- | --- | --- | --- |
|  | NPTII PCR | GUS PCR |  |  |
| pWVK211 | 14/25 | 15/24 | 100 | 2/10 (vascular-specific 2/10) |
| pWVK212 | 28/34 | 22/28 | 100 | 4/10 (vascular-specific 0/10) |

What is claimed is:

1. A plant transformed with the DNA construct comprising an isolated promoter consisting of any one of SEQ ID NO: 1 to 6 and functional variants having at least 98% sequence identity to SEQ ID NO: 1 to 6 operably linked to a desired nucleic acid, wherein said promoter regulates the expression of said desired nucleic acid.

2. The plant of claim 1, wherein the phenotype of said plant expresses a difference in lignin quality compared with a plant of the same species that is not transformed with said DNA construct.

3. The plant of claim 2, wherein the difference in lignin quality is characterized by change in the structure of the lignin molecule.

4. The plant of claim 1, wherein the phenotype of said plant comprises a difference in wood composition compared to a plant of the same species that is not transformed with said DNA construct.

5. A plant cell comprising a DNA construct comprising (i) an isolated promoter consisting of the sequence of any one of SEQ ID NO: 1 to 6 and functional variants having at least 98% sequence identity to SEQ ID NO: 1 to 6 and (ii) a desired nucleic acid, wherein said polynucleotide is operably linked to said desired nucleic acid.

6. A transgenic plant comprising the plant cell of claim 5.

7. A method for producing a transgenic plant, comprising (a) transforming a plant cell with a DNA construct that comprises (i) at least one isolated polynucleotide consisting of the sequence of any one of SEQ ID NOs. 1 to 6 and functional variants having at least 98% sequence identity to any one of SEQ ID NO: 1 to 6 and (ii) a desired nucleic acid, wherein said polynucleotide regulates the activity of said desired sequence; (b) culturing said transformed plant cell under conditions that promote growth of a plant, wherein said plant is a transgenic plant that exhibits a phenotype that is different from a plant of the same species that does not contain said DNA construct.

8. The method of claim 7, wherein the phenotype of said transformed plant is characterized by a difference in lignin quality compared to a plant of the same species that does not contain the DNA construct.

9. The method of claim 7, wherein the phenotype of the said transformed plant is characterized by a difference in fiber yield compared to a plant of the same species that does not contain the DNA construct.

10. The method of claim 7, wherein the phenotype of said transformed plant is characterized by a difference in plant cell development compared to a plant of the same species that does not contain the DNA construct.

11. A method for reducing lignin in a plant, comprising (a) introducing into a plant cell a DNA construct comprising (i) an isolated promoter consisting of the sequence of any one of SEQ ID NOs: 1 to 6 and functional variants having at least 98% sequence identity to any one of SEQ ID NO: 1 to 6 and (ii) a nucleic acid encoding a gene involved in lignin biosynthesis, wherein said nucleic acid is antisense relative to said promoter and wherein said promoter regulates the expression of said gene; (b) culturing said transformed plant cell under conditions that promote growth of a plant, wherein said plant is a transgenic plant that exhibits a phenotype that is different from a plant of the same species that does not contain said DNA construct; and (c) selecting a plant having reduced lignin content.

12. A method for increasing lignin in a plant, comprising (a) introducing into a plant cell a DNA construct comprising (i) an isolated promoter consisting of the sequence of any one of SEQ ID NOs: 1 to 6 and functional variants having at least 98% sequence identity to any one of SEQ ID NO: 1 to 6 and (ii) a nucleic acid encoding a gene involved in lignin biosynthesis, wherein said promoter regulates the expression of said gene; (b) culturing said transformed plant cell under conditions that promote growth of a plant, wherein said plant is a transgenic plant that exhibits a phenotype that is different from a plant of the same species that does not contain said DNA construct; and (c) selecting a plant having increased lignin content.

13. A method for obtaining wood, comprising (a) introducing into a plant cell of a woody plant a DNA construct comprising (i) an isolated promoter consisting of the sequence of any one of SEQ ID NOs: 1 to 6 and functional variants having at least 98% sequence identity to any one of SEQ ID NO: 1 to 6 and (ii) and a desired nucleic acid, wherein said promoter regulates the expression of said desired nucleic acid; (b) culturing said transformed plant cell under conditions that promote growth of a plant; and (c) obtaining wood from said plant.

14. The method of claim 13, wherein said woody plant is selected from a species of *Eucalyptus* or *Pinus*.

15. A method for obtaining wood pulp, comprising (a) introducing into a plant cell of a woody plant a DNA construct comprising (i) an isolated promoter consisting of the sequence of any one of SEQ ID NOs: 1 to 6 and functional variants having at least 98% sequence identity to any one of SEQ ID NO: 1 to 6 and (ii) and a desired nucleic acid, wherein said promoter regulates the expression of said desired nucleic acid; (b) culturing said transformed plant cell under conditions that promote growth of a plant; and (c) obtaining wood pulp from said plant.

16. The method of claim 15, wherein said woody plant is selected from a species of *Eucalyptus* or *Pinus*.

* * * * *